US011076762B2

(12) United States Patent
Vaschillo et al.

(10) Patent No.: US 11,076,762 B2
(45) Date of Patent: Aug. 3, 2021

(54) METHODS AND APPARATUS FOR EXPRESS ESTIMATION OF THE ARTERIAL ELASTIC PROPERTY IN A SUBJECT

(71) Applicant: Rutgers, The State University of New Jersey, New Brunswick, NJ (US)

(72) Inventors: Evgeny G. Vaschillo, Edison, NJ (US); Bronya Vaschillo, Edison, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 441 days.

(21) Appl. No.: 15/919,757

(22) Filed: Mar. 13, 2018

(65) Prior Publication Data

US 2018/0263506 A1 Sep. 20, 2018

Related U.S. Application Data

(60) Provisional application No. 62/470,820, filed on Mar. 13, 2017.

(51) Int. Cl.
*A61B 5/02* (2006.01)
*A61B 5/021* (2006.01)
(Continued)

(52) U.S. Cl.
CPC ........ *A61B 5/02007* (2013.01); *A61B 5/0205* (2013.01); *A61B 5/02108* (2013.01);
(Continued)

(58) Field of Classification Search
CPC .............. A61B 5/02007; A61B 5/0205; A61B 5/02108; A61B 5/0456; A61B 5/7246;
(Continued)

(56) References Cited

U.S. PATENT DOCUMENTS

| 5,997,482 A | * | 12/1999 | Vaschillo | ........... | A63B 71/0686 600/484 |
| 2004/0116784 A1 | * | 6/2004 | Gavish | ............... | A61B 5/14551 600/300 |

(Continued)

OTHER PUBLICATIONS

Pitzalis et al., "Effect of respiratory rate on the relationships between RR interval and systolic blood pressure fluctuations: a frequency-dependent phenomenon," Cardiovascular Research, vol. 38, Issue 2, May 1998, pp. 332-339 (Year: 1998).*

(Continued)

*Primary Examiner* — Devin B Henson
*Assistant Examiner* — Justin Xu
(74) *Attorney, Agent, or Firm* — Fox Rothschild LLP

(57) ABSTRACT

Methods and systems for express estimation of the arterial elasticity in a subject are presented. The methods and systems provide simplicity in measurement and the opportunity to measure the arterial elasticity through HRV. The method includes imposing a rhythmical stimulation at a frequency between about 0.06 Hz and 0.081 Hz to cause an oscillation on the cardiovascular system of a subject. The method further include measuring a response associated with the oscillation on the cardiovascular system and determining the arterial elasticity of the subject based on a level of the response associated with the oscillation.

16 Claims, 24 Drawing Sheets

(51) Int. Cl.
   *A61B 5/00*    (2006.01)
   *A61B 5/0205*  (2006.01)
   *A61B 5/352*   (2021.01)
   *A61B 5/022*   (2006.01)
   *A61B 5/0225*  (2006.01)

(52) U.S. Cl.
   CPC ............ *A61B 5/352* (2021.01); *A61B 5/7246* (2013.01); *A61B 5/7257* (2013.01); *A61B 5/02225* (2013.01); *A61B 5/02255* (2013.01)

(58) Field of Classification Search
   CPC .............. A61B 5/7257; A61B 5/02225; A61B 5/02255
   See application file for complete search history.

(56) References Cited

U.S. PATENT DOCUMENTS

2005/0124906 A1*  6/2005  Childre .............. A61B 5/02405
                                              600/529
2005/0209521 A1*  9/2005  Kettunen ........... A61B 5/02405
                                              600/508
2007/0100246 A1*  5/2007  Hyde .................. A61B 5/0452
                                              600/509
2010/0174205 A1*  7/2010  Wegerif ............... A61B 5/0456
                                              600/515
2018/0263567 A1*  9/2018  Beise .................. A61B 5/4035

OTHER PUBLICATIONS

Vaschillo (2002, "Heart Rate Variability Biofeedback as a Method for Assessing Baroreflex Function: A Preliminary Study of Resonance in the Cardiovascular System") (Year: 2002).*

Vaschillo, et al: "Heart Rate Variability Biofeedback as a Method for Assessing Baroreflex Function: A Preliminary Study of Resonance in the Cardiovascular System", Applied Psychophysiology and Biofeedback, Mar. 2002, vol. 27, No. 1, pp. 1-27.

Vaschillo, et al: "Early Signs of Cardiovascular Dysregulation in Young Adult Binge Drinkers", Wiley Psychophysiology, 2017, pp. 1-13.

* cited by examiner

200

Perform operations by a computing device to continuously measure beat-to-beat intervals of a person, convert the measured intervals into respective electrical heartrate signals, and record them
202

Give instructions for a person to produce sighs following the rhythmical reference visual, sound or tactile signal
204

Start to rhythmically display a reference signal at a frequency of 0.066 Hz on the computing device
206

Select part of the electrical heartrate signals recorded during sighing and generate an equidistant waveform heartrate signal by (a) cubic interpolating the beat-to-beat intervals and (b) resampling the interpolated beat-to-beat intervals at a rate of 4 Hz
208

Performing operations by the computing device to calculate an FFT spectrum of the equidistant waveform heartrate signal for the sighing period
210

Measuring the level of arterial elasticity as a power of the FFT spectrum at a reference frequency
212

*FIG. 2*

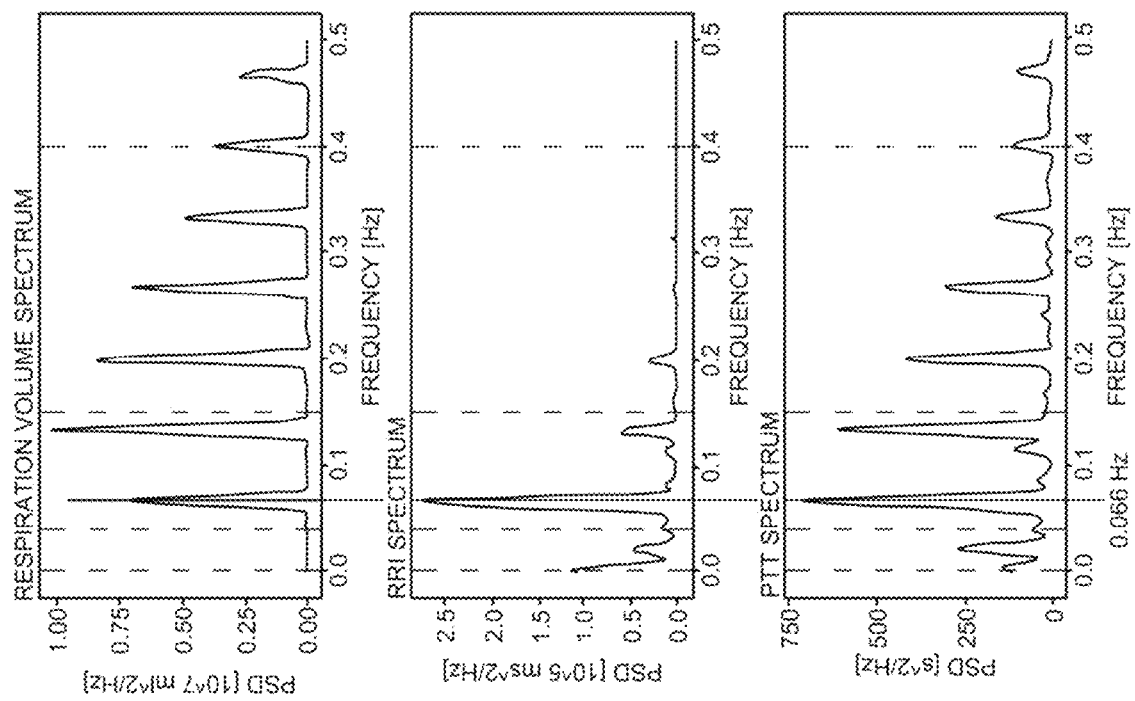
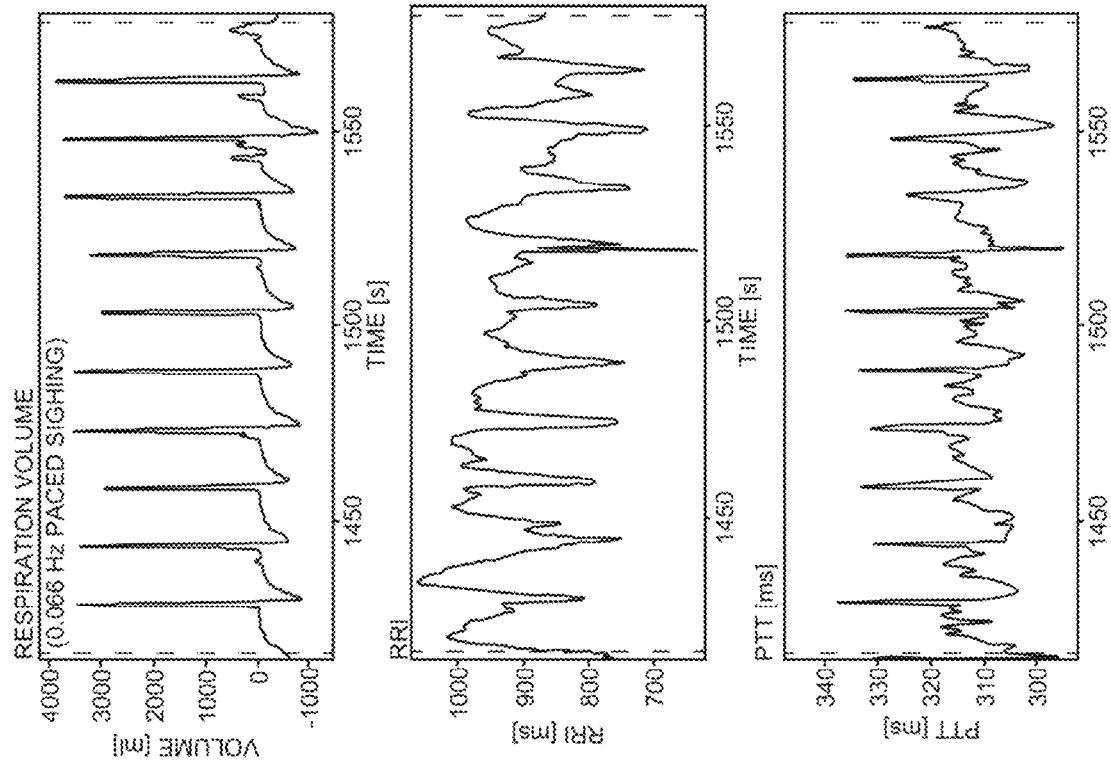
FIG. 3A
FIG. 3B

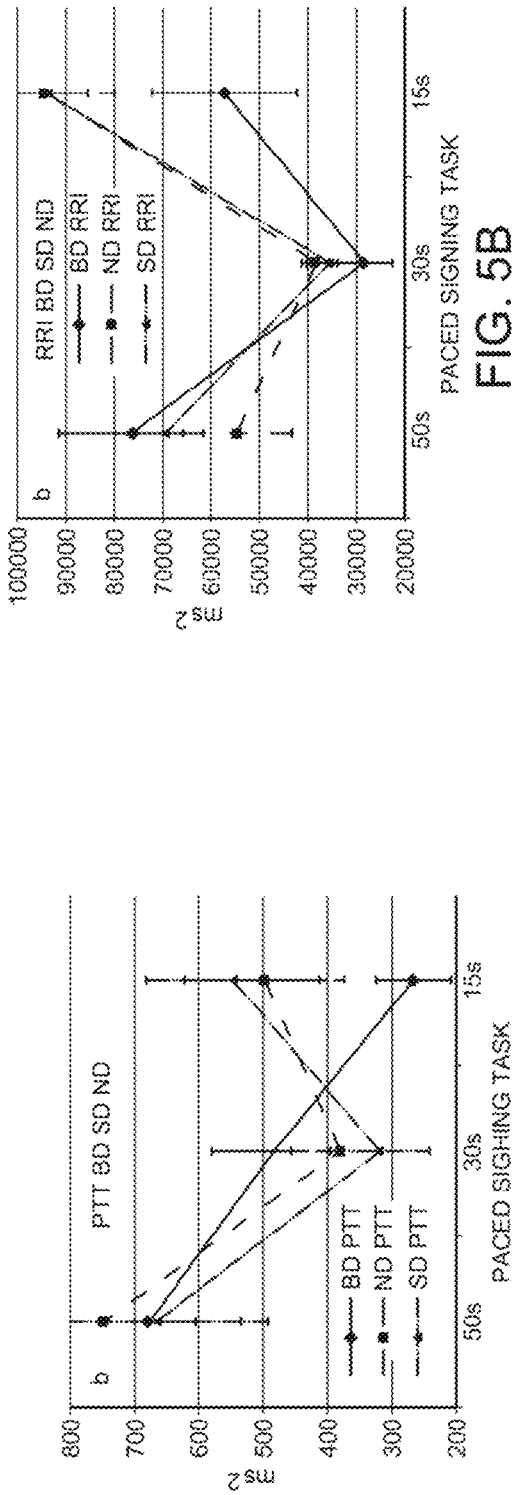
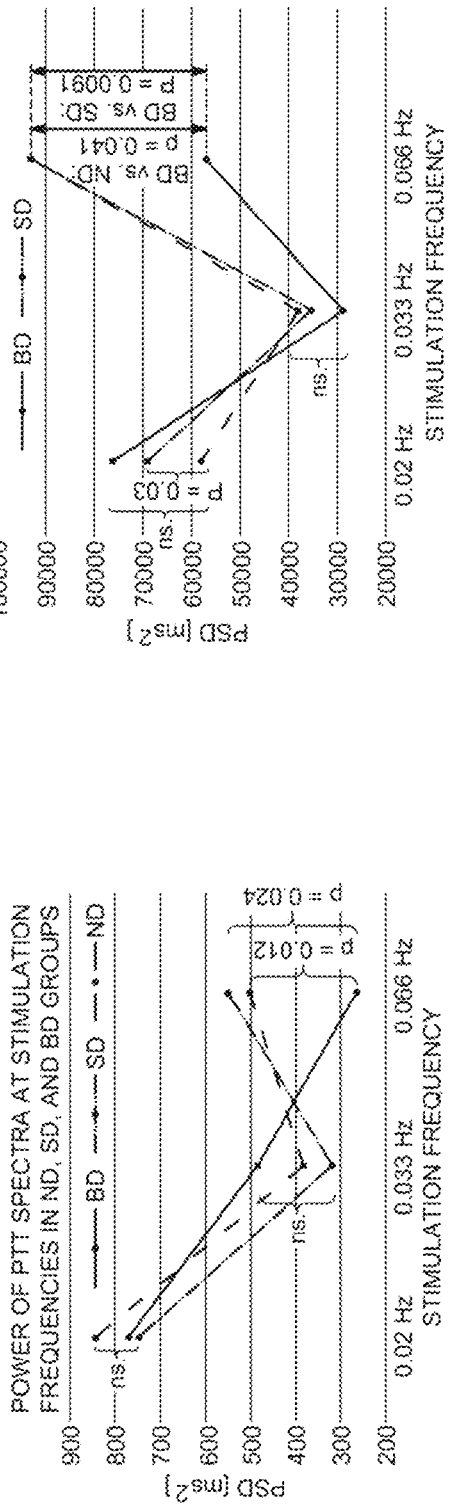
FIG. 5A
FIG. 5B
FIG. 5C
FIG. 5D

FIG. 13A
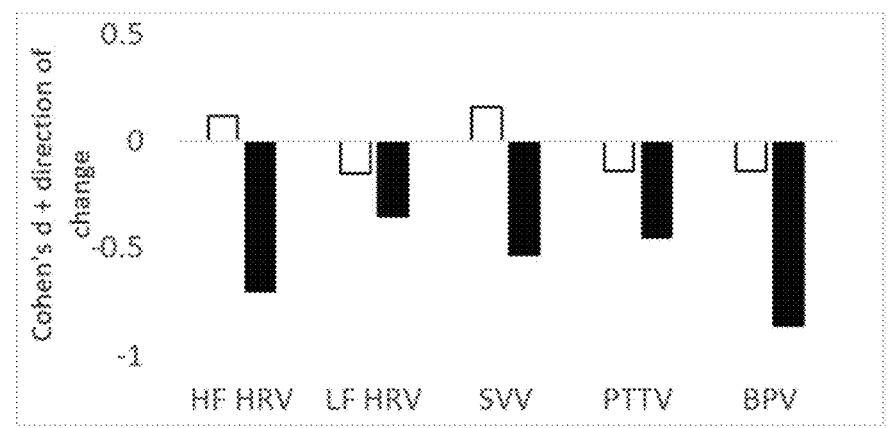
FIG. 13B
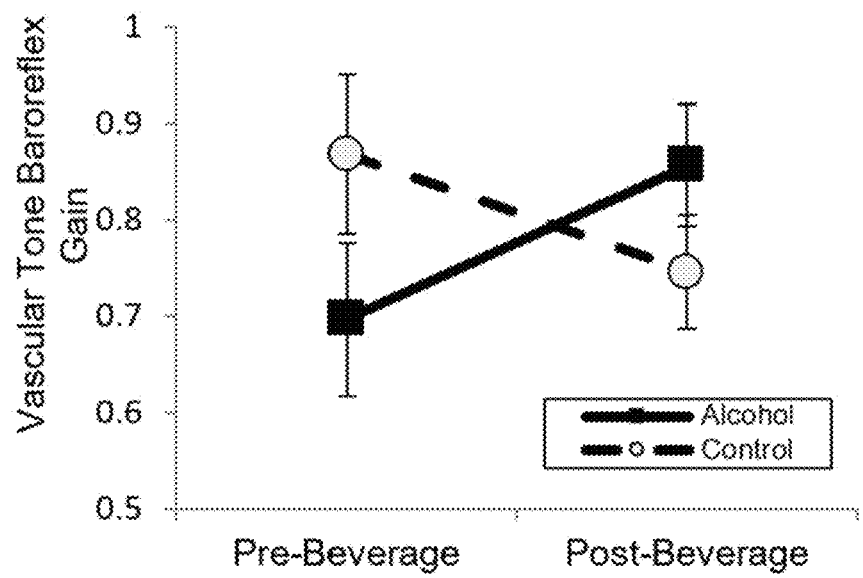
FIG. 13C
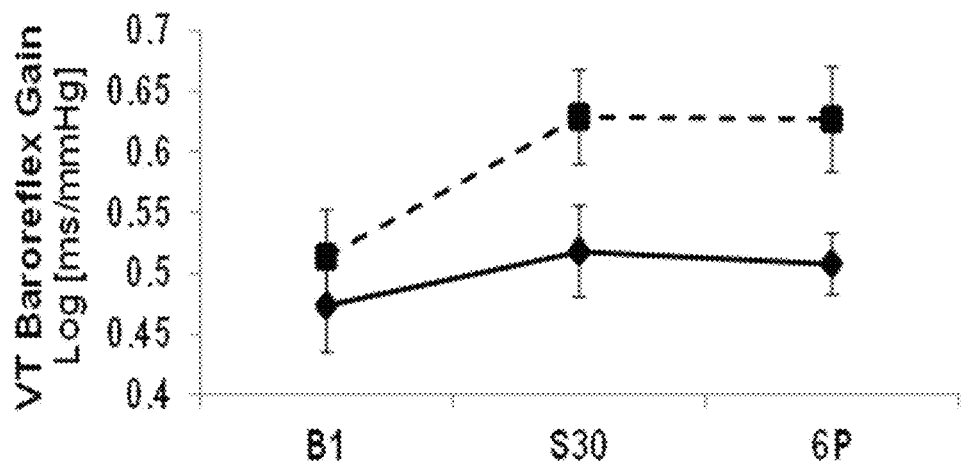
*FIG. 13*

FIG. 15A
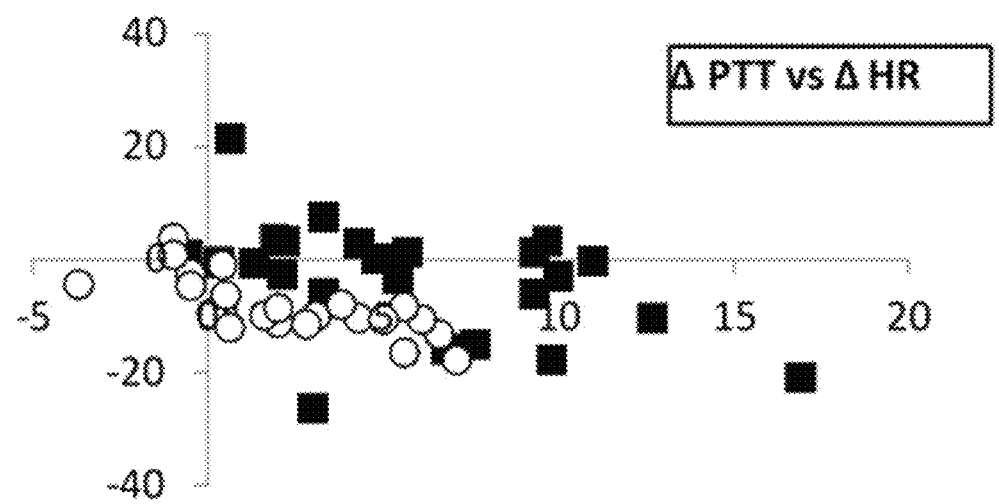
FIG. 15B
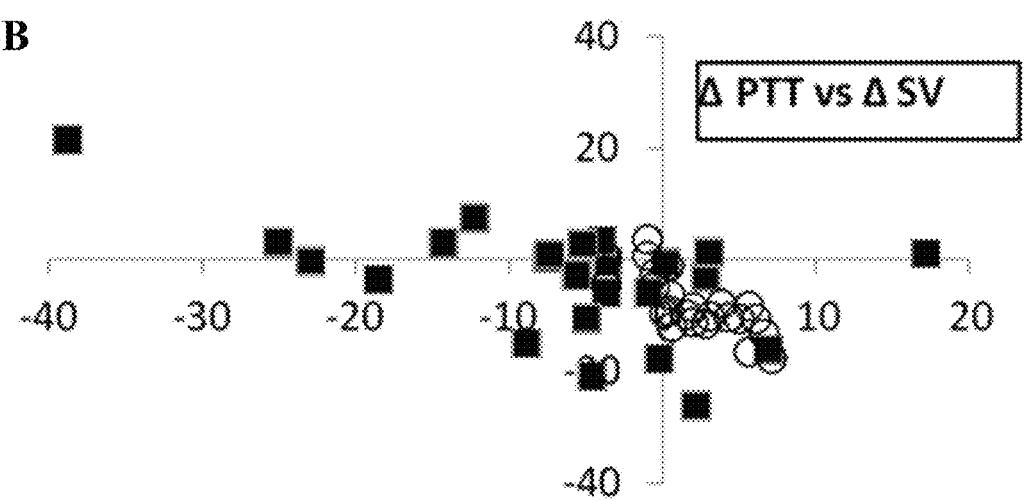
FIG. 15C
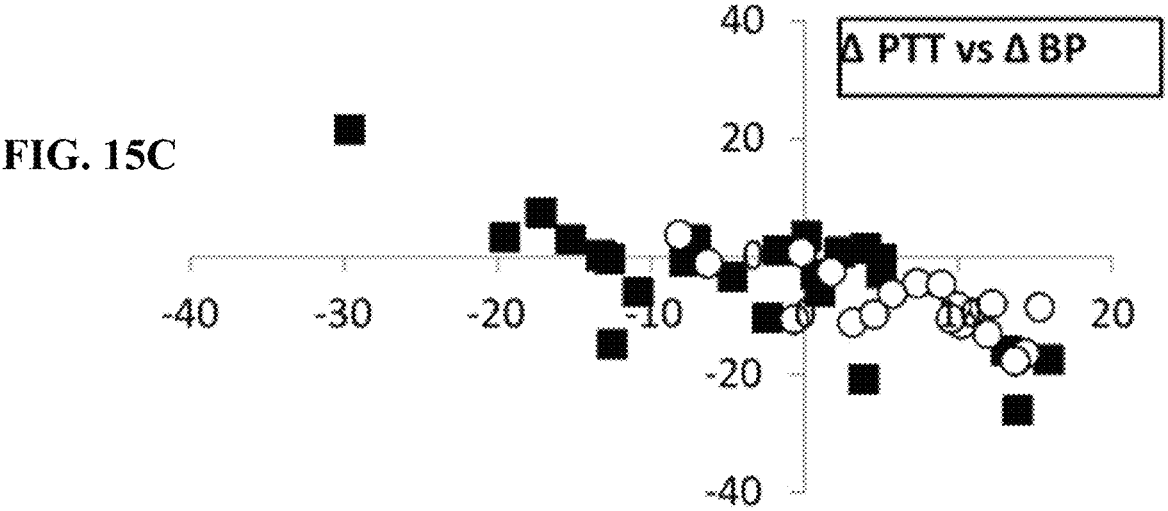
*FIG. 15*

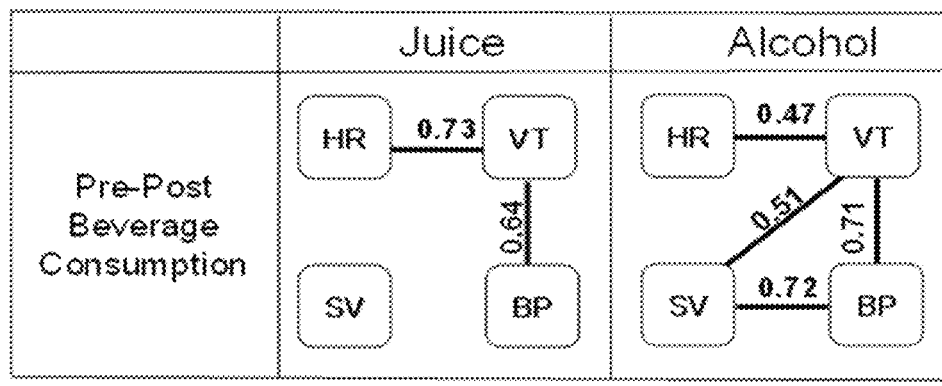
FIG. 16A
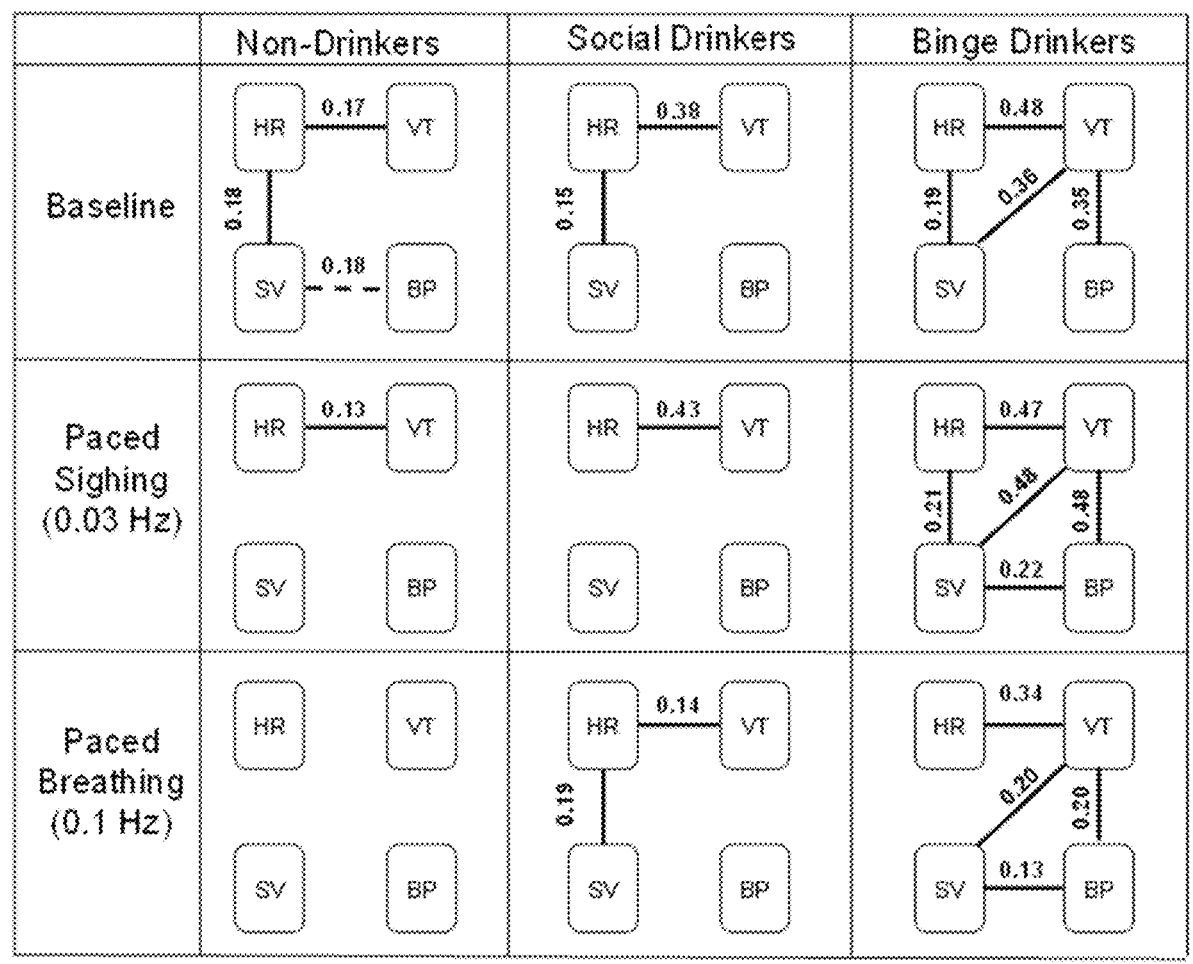
FIG. 16B
*FIG. 16*

METHODS AND APPARATUS FOR EXPRESS ESTIMATION OF THE ARTERIAL ELASTIC PROPERTY IN A SUBJECT

CROSS-REFERENCE TO RELATED APPLICATIONS

This application claims priority under 35 U.S.C. § 119(e) to U.S. Provisional Patent Application No. 62/470,820, filed Mar. 13, 2017. The foregoing applications are incorporated by reference herein.

GOVERNMENT INTERESTS

The invention disclosed herein was made, at least in part, with government support under Grant No. R21AA020367 from National Institute on Alcohol Abuse and Alcoholism (NIAAA). Accordingly, the U.S. Government has certain rights in this invention.

FIELD

This disclosure relates generally to systems and methods for evaluating vessel conditions and more specifically relates to express estimation of the arterial elastic property in a person.

BACKGROUND

Reduced arterial elasticity is known to be associated with cardiovascular risk factors (e.g., hypertension, metabolic syndrome, diabetes, advanced renal failure, hypercholesterolemia, obesity) and increased stress level. Heavy alcohol consumption is known to affect the cardiovascular system in a negative way, including the reduced arterial elasticity/ increased stiffness. Conventional methods for evaluating arterial elasticity are inconvenient since measurements request sophisticated and expensive equipment.

Chronic heavy alcohol use is a well-established risk factor for cardiovascular events in middle age, such as stroke, sudden death, myocardial infarction, and progression of atherosclerosis. Early clinical manifestations of cardiovascular risk are also evident in young binge drinkers. Specifically, flow-mediated and nitroglycerin-mediated dilation were significantly lower among young adult binge drinkers compared to the same aged alcohol abstainers. This suggests that even early in an individual's drinking history, repeated binge drinking episodes may lead to endothelial dysfunction, vascular tone dysregulation, and consequently, diminished arterial elasticity, which can serve as early prognostic indicators of future cardiovascular disorders.

Little is known about the early stage impacts of hazardous alcohol use. Acute alcohol intoxication invokes multiple reversible cardiovascular responses that allow the body to adapt to the presence of alcohol, but the possibility of early stage vascular dysfunction raises the question of how and when adaptive cardiovascular reactions to acute alcohol give rise to alcohol-related system dysfunction. This is particularly important considering that more than a half of college student drinkers engage in regular binge drinking.

SUMMARY

The present disclosure provides methods and systems for express estimation of arterial elasticity in a subject. The methods and systems provide simplicity in measurement and the opportunity to measure the arterial elasticity through HRV. The method may include imposing a rhythmical stimulation at a frequency between about 0.06 Hz and about 0.081 Hz to cause an oscillation on the cardiovascular system of a subject. The method may further include measuring a response associated with the oscillation on the cardiovascular system and determining an arterial elasticity of the subject based on a level of the response associated with the oscillation. In some embodiments, the response is beat-to-beat intervals (time intervals between individual heart beats). In some embodiments, the rhythmical stimulation is a sympathetic challenge. In some embodiments, the sympathetic challenge is a paced sighing sympathetic challenge.

The method may also include providing the subject a rhythmical reference cue and causing the subject to perform a paced sighing in response to the rhythmical reference cue, whereby the paced sighing imposes the rhythmical stimulation on the cardiovascular system of the subject. The rhythmical reference cue can be a visual cue, an audio cue, or a tactile cue.

The method may further include measuring beat-to-beat intervals of the subject and generating an equidistant waveform based on the beat-to-beat intervals. The method may include generating a frequency domain spectrum from the equidistant waveform by a fast Fourier transform (FFT). The method may also include determining a power spectrum density of the frequency domain spectrum at a reference frequency. In some embodiments, the reference frequency is about 0.066 Hz or about 0.081 Hz.

Steps of generating the equidistant waveform may include performing cubic interpolation for the beat-to-beat intervals of the subject and resampling the interpolated beat-beat intervals at a rate of 4 Hz. The beat-to-beat intervals can be measured from a signal from an electrocardiogram (ECG or EKG), plethysmograph, or photoplethysmography (PPG).

In one aspect, a method of assessing arterial elasticity of a subject includes imposing a paced sighing sympathetic challenge at a frequency between about 0.06 Hz and about 0.081 Hz to cause an oscillation on the cardiovascular system of the subject. The method also includes measuring a pattern of beat-to-beat intervals in response to the oscillation on the cardiovascular system of the subject and determining an arterial elasticity of the subject based on the pattern of the beat-to-beat intervals in response to the oscillation.

In another aspect, a method of evaluating an impact of alcohol consumption on a subject is provided. The method is based on a correlation between a drinking profile and the assessment of the arterial elasticity according to the above-disclosed method. The drinking profile may include years of alcohol use of the subject.

In yet another aspect, a system for assessing arterial elasticity is disclosed. The system may impose a rhythmical stimulation at a frequency between about 0.06 Hz and about 0.081 Hz to cause an oscillation on the cardiovascular system of a subject. The system may also measure a response associated with the oscillation on the cardiovascular system of the subject and determine an arterial elasticity of the subject based on a level of the response associated with the oscillation. In some embodiments, the rhythmical stimulation is a sympathetic challenge. In some embodiments, the sympathetic challenge is a paced sighing sympathetic challenge.

In some embodiments, the system may provide the subject a rhythmical reference cue and cause the subject to perform a paced sighing in response to the rhythmical reference cue, whereby the paced sighing imposes the rhythmical stimulation on the cardiovascular system of the subject.

The system may also measure beat-to-beat intervals of the subject and generate an equidistant waveform based on the beat-to-beat intervals. The system may also generate a frequency domain spectrum from the equidistant waveform by a fast Fourier transform (FFT). In generating the equidistant waveform, the system may perform cubic interpolation for the beat-to-beat intervals of the subject and resample the interpolated beat-beat intervals at a rate of 4 Hz. The system may further determine a power spectrum density of the frequency domain spectrum at a reference frequency. The frequency can be about 0.066 Hz or about 0.081 Hz.

DESCRIPTION OF THE DRAWINGS

The present solution will be described with reference to the following drawing figures, in which like numerals represent like items throughout the figures.

FIG. 2 shows an embodiment of a process for express estimation of arterial elasticity of a subject.

FIGS. 3A and 3B (collectively "FIG. 3") show measurements of the cardiovascular parameters in response to paced sighing at a frequency of 0.066 Hz (15 sec between sighs). FIG. 3A shows measurements of heart stroke volume, RRI, and PTT; and FIG. 3B shows power spectral density ("PSD") values at a range of frequencies corresponding the measurements in FIG. 3A.

FIGS. 5A, 5B, 5C and 5D show responses of the HR and VT control systems to the stimulation. FIG. 5A shows oscillations of PTT for ND, SD, and BD in paced sighing tasks at 0.02, 0.03, and 0.066 Hz; FIG. 5B shows oscillations of RRI for ND, SD, and BD in paced sighing tasks at 0.02, 0.03, and 0.066 Hz; FIG. 5C shows averaged across group power of PTT for ND, SD, and BD in paced sighing tasks at 0.02, 0.03, and 0.066 Hz; and FIG. 5D shows averaged across group power of PTT for ND, SD, and BD in paced sighing tasks at 0.02, 0.03, and 0.066 Hz.

FIGS. 13A, 13B and 13C (collectively "FIG. 13") show effects of alcohol consumption on VT BRS Gain. FIG. 13A shows the effect size (Cohen's d) of pre- to post-beverage changes in cardiovascular variability pre- to post-consumption of a juice (white) or alcohol (black) beverage. (d>0 implies increases, d<0 implies decreases); FIG. 13B shows VT BRS Gain measured as blood pressure ("BP") before and after alcohol use; and FIG. 13C shows VT BRS Gain in BP in SD and BD in B1, S30, and 6P tasks.

FIGS. 15A, 15B and 15C (collectively "FIG. 15") show interrelated cardiovascular response to alcohol, with a comparison between alcohol (black) and juice (white) in causing changes in individual processes and increased coupling of vascular changes (Y-axis) to HR (FIG. 15A), stroke volume (FIG. 15B) and BP (FIG. 15C) changes.

FIGS. 16A and 16B (collectively "FIG. 16") show coupling among cardiovascular processes before and after alcohol use (FIG. 16A) and for ND, SD, and BD at rest and under loading (FIG. 16B).

DETAILED DESCRIPTION

Figure 1:
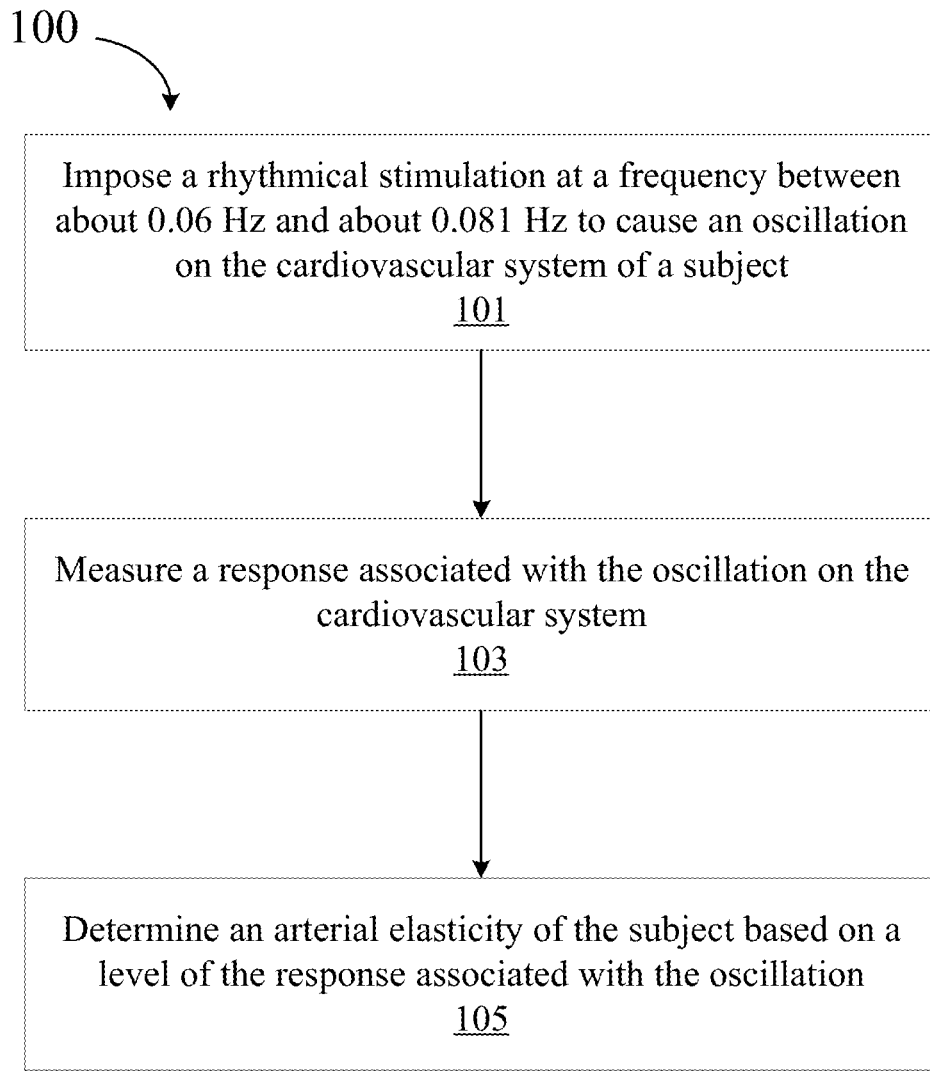
FIG. 1 shows an example of a process for express estimation of arterial elasticity of a subject.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

Abnormal vascular dynamics have far-reaching consequences due in part to the vascular tone baroreflex, which uses variability in blood vessel diameter to compensate for acute shifts in blood pressure and modulate stress reactions. The vascular tone baroreflex is a closed-loop system that functions via information exchange between the autonomic and central nervous systems. Thus, it is possible to observe the interrelationship of the physiological and neurological processes that support emotional self-regulation and stress responding by directly assessing vascular tone baroreflex activity. By comparing vascular tone baroreflex sensitivity in nondrinkers, moderate drinkers, and heavy drinkers, it is possible to observe how alcohol disrupts these interrelated processes and instigates the cascade of self-regulatory failures that enhance risk for using alcohol to cope with emotional dysregulation. Little is known about the vascular tone baroreflex system because, until recently, non-invasive assessment of changes in beat-to-beat vascular tone in response to perturbations was not accurate. The present solution uses new technology and new methodologies to validly characterize basic functional properties of the vascular tone baroreflex system.

The capability of detecting early pathophysiological conditions is crucial to the prevention and/or successful treatment of a disease. Arterial elasticity (or arterial stiffness) is an important indicator of existing cardiovascular risks in an otherwise healthy individual. Changes in arterial elasticity have been linked to systolic hypertension in elders. The present solution relates to a simple method of evaluating arterial elasticity by monitoring beat-to-beat heart rate intervals while performing sighing at 0.06-0.08 Hz (16.7-12.5 seconds between sighs), analyzing beat-to-beat heart rate intervals, generating a frequency spectrum via a fast Fourier transform ("FFT").

In some scenarios, the reference power spectral density ("PSD") at 0.06-0.08 Hz or 0.066 Hz for a healthy population (non-drinker and social drinker) will be used as a baseline to which the PSD at the same frequency determined for a test subject shall be compared. A statistically significant deviation (e.g., reduction) from the baseline indicates reduced arterial elasticity. In addition, a baseline PSD value can be established for an individual. PSD can be determined on a daily basis. A statistically significant reduction of daily PSD as compared to the baseline indicates reduced cardiovascular health and/or increased stress level.

Accordingly, the present document describes an easy and simple method to evaluate a current level of elasticity of the arteries in a person. The evaluation is provided using a reaction of the vessels to rhythmical sighing which affects all arteries. Methods that can be used to obtain beat-to-beat intervals of heart rate ("HR") of a person for the evaluation of arterial elasticity include ECG, plethysmograph, photoplethysmography (PPG), and ultrasound. Heart rate measurements can be taken at various locations of the body, such as a finger, low arm, and upper arm. In some conventional solutions for monitoring arterial stiffness, pulse transit time ("PTT") measurements are made (i.e., the time it takes for the pulse pressure waveform to travel from one arterial location to another). PTT is determined based on pulse pressure waveform measurements taken at two separate locations.

In some embodiments, the present method (1) estimates the level of arterial stiffness using beat-to-beat intervals of heart rate (e.g., R-to-R time intervals ("RRI") determined from ECG recordings) information collected during paced sighing at reference frequency in the range of 0.06-0.081 Hz or at 0.066 Hz; (2) generates an equidistant waveform of beat-to-beat heart rate intervals signal; (3) calculates a frequency spectrum via FFT; and (3) compares power spectral density (PSD) at a reference frequency in the range of 0.06-0.081 Hz or 0.066 Hz in healthy population (non-drinker and social drinker) to a PSD at the same frequency determined for a test subject. A statistically significant deviation (reduction) from the baseline (i.e., the reference PSD) indicates reduced arterial elasticity. RRI can be determined from EKG, pulse pressure waveform.

The methods of the present solution involve: recording two and a half (2.5) minutes (depending on the frequency of sighing, the recording period could be shorter or longer) of heart rate while the individual performs a paced sighing task at a reference frequency; calculating a spectrum of heart rate variability; and determining a spectral parameter associated with the elasticity of arteries. The spectral parameter can be used as a biomarker to estimate a current level of arterial elasticity in the person.

An implementing apparatus includes a bio-amplifier, a pacer, and a microprocessor. The bio-amplifier collects an electrocardiogram ("ECG"). The pacer sets the rate for a rhythmical sighing task. The microprocessor measures heart beat-to-beat time intervals, collects the sequence of heart beat-to-beat time intervals, calculates a frequency spectrum of the heart beat-to-beat sequence, and finds a parameter that reflects a current level of elasticity of the arteries in the person.

The present solution can be used in a variety of applications. For example, the present solution is used to: (1) estimate the level of development of atherosclerosis and other vascular diseases associated with arterial stiffness; (2) perform daily monitoring of arterial elasticity (e.g., based on beat-to-beat heart rate interval measurements taken during paced sighing at 0.06-0.08 Hz (16.7-12.5 seconds between sighs) using ECG, pulse pressure waveform (plethysmograph), or heart rate monitoring application on a smart phone (photoplethysmograph), etc.); (3) provide express medical screening of large groups of people for status of vascular conditions; and/or (4) detect early signs of disorder in the cardiovascular system (for example, detect early stages of cardiovascular disregulation caused by intensive alcohol use).

Exemplary Processes for Evaluating the Arterial Elastic Property

Smooth muscles that are located in the vessels' walls continuously alter the diameter of the vessels adapting an organism to constantly changing conditions of the internal and external environment. The degree of the smooth muscle contraction determines the diameter of the vessel and vascular tone ("VT"). The pulse transit time ("PTT") can be used to evaluate the mean value of the VT ("Mean VT") over a given period of time as well as the VT variability using frequency spectrum calculated over the same time period. Artery elasticity is related to VT variability.

To evaluate arterial elasticity, researchers usually simultaneously measure spontaneous oscillations in the blood pressure, in the finger photoplethysmogram (PPG) or in PTT. It is known that the working frequency range of the VT control system is about 0.02-0.08 Hz. Spontaneous VT oscillations in this range do not always have enough magnitude to evaluate arterial elasticity.

The present solution provides a method to impose oscillations on the cardiovascular system in the desired range. Rhythmical paced sighing produces high-amplitude oscillation in PTT, BP, and RRI. It has been shown that the amplitude of PTT and RRI oscillations at 0.066 Hz was significantly lower in people with reduced arterial elasticity. Each sigh abruptly caused short-time vasodilatation, therefore paced rhythmical sighing produced high PTT oscillation at the desired frequency and triggered baroreflex which produced RRI oscillation. Elasticity reduction decreased the sensitivity of the baroreceptors and consequently the amplitude of RRI oscillation.

FIG. 1 shows an example of a process 100 for express estimation of arterial elasticity of a subject. The process 100 begins at 101 with imposing a rhythmical stimulation at a frequency between about 0.06 Hz and about 0.081 Hz to cause an oscillation on the cardiovascular system of a subject. In some embodiments, the frequency is about 0.066 Hz or about 0.081 Hz. In some embodiments, the process includes providing the subject a rhythmical reference cue and causing the subject to perform a paced sighing or a paced breathing in response to the rhythmical reference cue, whereby the paced sighing or the paced breathing imposes the rhythmical stimulation on the cardiovascular system of the subject. In some embodiments, the rhythmical reference cue is a visual cue, an audio cue or a tactile cue. In some embodiments, the rhythmical stimulation is a sympathetic challenge or a parasympathetic challenge. The sympathetic challenge may be a paced sighing sympathetic challenge, and the parasympathetic challenge is a paced breathing parasympathetic challenge. In some embodiments, the response associated with the oscillation on the cardiovascular system is beat-to-beat intervals. The beat-to-beat intervals can be measured from a signal from an electrocardiogram (ECG or EKG), plethysmograph, or photoplethysmography (PPG).

At 103, the process includes measuring a response associated with the oscillation on the cardiovascular system of the subject. The process may include measuring beat-to-beat intervals of the subject and generating an equidistant waveform based on the beat-to-beat intervals. The process may further include generating a frequency domain spectrum from the equidistant waveform by a fast Fourier transform (FFT). In generating a frequency domain spectrum from the equidistant waveform, the process may include performing cubic interpolation for the beat-to-beat intervals of the subject and resampling the interpolated beat-beat intervals at a rate of 4 Hz. At 105, the process continues with determining an arterial elasticity of the subject based on a level of the response associated with the oscillation. The process may also include determining arterial elasticity of the subject by determining a power spectrum density of the frequency domain spectrum at a reference frequency. The reference frequency refers to the frequency at which the rhythmical stimulation of the cardivascular system is performed.

Referring now to FIG. 2, an exemplary method 700 for evaluating the vascular elastic property in a subject is provided. Rhythmical sighing stimulates the CardioVascular System ("CVS") imposing oscillation at stimulation frequency on the vessels diameter that rhythmically dilates—constricts. To evaluate arterial elasticity, paced sighing at a frequency in the range of 0.06-0.08 Hz (16.7-12.5 sec between sighs) can be used. This range is the upper part of the working range of the VT control system (0.02-0.08 Hz). If the stimulation frequency lies in the range of 0.06-0.08 Hz, the amplitude of elicited oscillation in vessels diameter depends on the level of arterial elasticity since vessels with pure elasticity cannot change diameter fast. The vessel's diameter oscillation modulates the afferent stream from baroreceptors located in the vessels walls. This afferent stream in turn through baroreflex modulates oscillation in RRIs. Therefore, the amplitude of RRI oscillation at stimulated frequency depends on arterial elasticity.

As shown in FIG. 2, the process 200 begins with 202 where operations are performed by a computing device to continuously measure beat-to-beat intervals of a person. The beat-to-beat intervals are converted into respective electrical heart rate signals. The electrical heart rate signals are recorded. Next, in 204, instructions are given for a person to produce signs following a rhythmical reference visual, sound or tactile signal.

A rhythmical display of a reference signal is started in 206. The reference signal is rhythmically displayed on the computing device at a frequency of 0.066 Hz. The reference signal comprises a periodic signal (e.g., sinusoidal signal that completes a pattern within a measuring time frame (called a period) and repeats the pattern over identical subsequent periods) indicating a sigh interval to a subject (i.e., indicating when the subject is to output a sigh so as to produce a sequence of sighs having a particular frequency).

Next, in 208, a part of the electrical heart rate signals recorded during sighing are selected. An equidistant waveform heartrate signal is then generated by (a) cubic interpolating the beat-to-beat intervals and (b) resampling the interpolated beat-to-beat intervals at a rate of 4 Hz. The computing device then performs operations in 212 to calculate an FFT spectrum of the equidistant waveform heartrate signal for the sighing period. The power of spectrum at reference frequency can also be calculated in accordance with the following Equations (1) and (2).

$$C(\omega_i) = \frac{2}{U_0 T} \int_0^T Y(t)\sin(\omega_i t)dt \quad (1)$$

$$D(\omega_i) = \frac{2}{U_0 T} \int_0^T Y(t)\cos(\omega_i t)dt \quad (2)$$

$$T = KT_i, \ T_i = 2\pi/\omega_i, \ \omega_i = 2\pi f_i$$

where t is the current time (sec), $f_i$ is the frequency of the $i^{th}$ target stimulus sinusoidal signal (Hz), T is the time of the task (e.g., 5 minutes), K is an integer, Y(t) is the physiological measure (e.g., HR, BP and RC), and $U_o$ is the amplitude of the stimulus sinusoidal signal. Using $C(\omega_i)$ and $D(\omega_i)$, the power of spectrum is calculated at reference frequency $A(\omega_i)$ of the observed process as in Equation (3):

$$A(\omega_i) = \sqrt{C(\omega_i)^2 + D(\omega_i)^2} \quad (3)$$

This algorithm allows reducing the error of calculation when the duration of the observed process is short. In the present case, the duration is ten full periods only.

In 212, the level of personal artery elasticity is measured as a power of the FFT spectrum at a reference frequency. For example, the peak of the frequency spectrum of the equidistant waveform heartrate signal indicates the level of personal artery elasticity. A lower the peak indicates a low personal artery elasticity. A higher the peak indicates a high personal artery elasticity. A threshold value equal to 60000 $ms^2$ can be used. This threshold value lies between values of power RRI spectrum in BD and ND/SD groups (see FIG. 5A). The level of personal artery elasticity can indicate a level of stress, hypertension and/or general health of a cardiovascular system.

The following EXAMPLES are provided for purposes of explaining in more detail the present solution. The present solution is not limited to the contents of EXAMPLES.

Example 1

Cardiovascular data has been collected from 71 young (18-24 yrs) healthy individuals divided into 3 groups according to their alcohol consumption: Binge Drinker ("BD") (24 binge drinkers), Social Drinker ("SD") (23 social drinkers), and Non-Drinkers ("ND") (24 non-drinkers) following the process shown below:

a) performing a 5-minute physiological recording while performing paced sighing task, i.e., beat-to-beat intervals are determined from an electrocardiogram (ECG), plethysmograph, photoplethysmography (e.g., heart rate captured by cameras on a mobile device), and/or time intervals between pulse pressure waveform;

b) generating a frequency spectrum for beat-to-beat intervals (e.g., RRI) and PTT;

c) comparing the amplitude of the frequency power at different sighing pace (0.02 Hz (every 50 sec), 0.033 Hz (every 30 sec) and 0.066 Hz (every 15 sec)); and d) correlating the lack of spectral response to sighing at 0.066 Hz in RRI to the similar lack of response in PTT in the binge drinking group. Since binge drinking is associated with increased arterial stiffness and thus reduced PTT, therefore the RRI data can also be utilized to predict arterial elasticity.

Figure 4A:
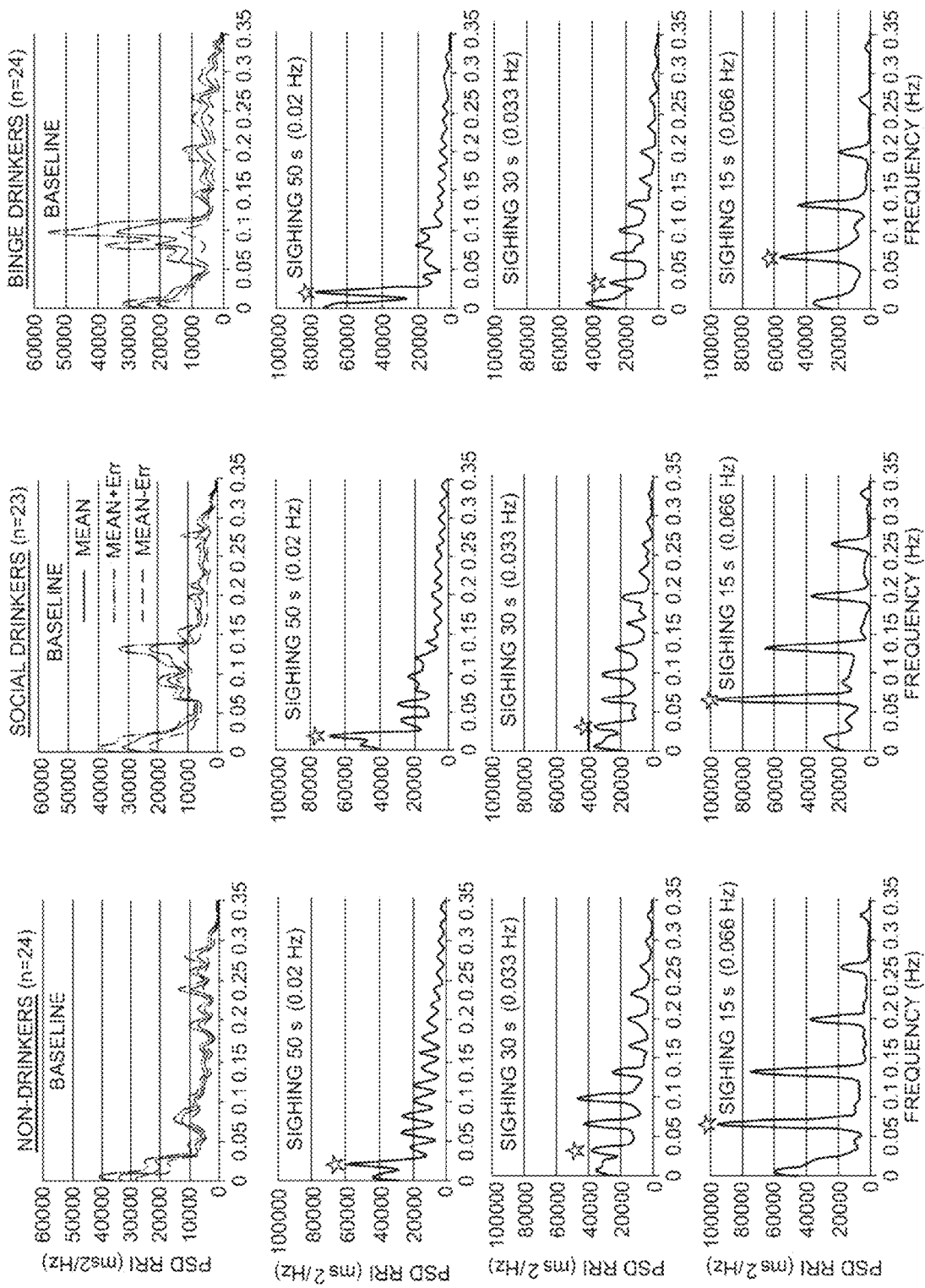
FIGS. 4A and 4B (collectively "FIG. 4") show RRI spectra (FIG. 4A) and PTT spectra (FIG. 4B) averaged by nondrinker ("ND"), social drinkers ("SD"), and binge drinkers ("BD") in baseline and in paced sighing tasks at 0.02, 0.03, and 0.066 Hz.
Figure 4B:
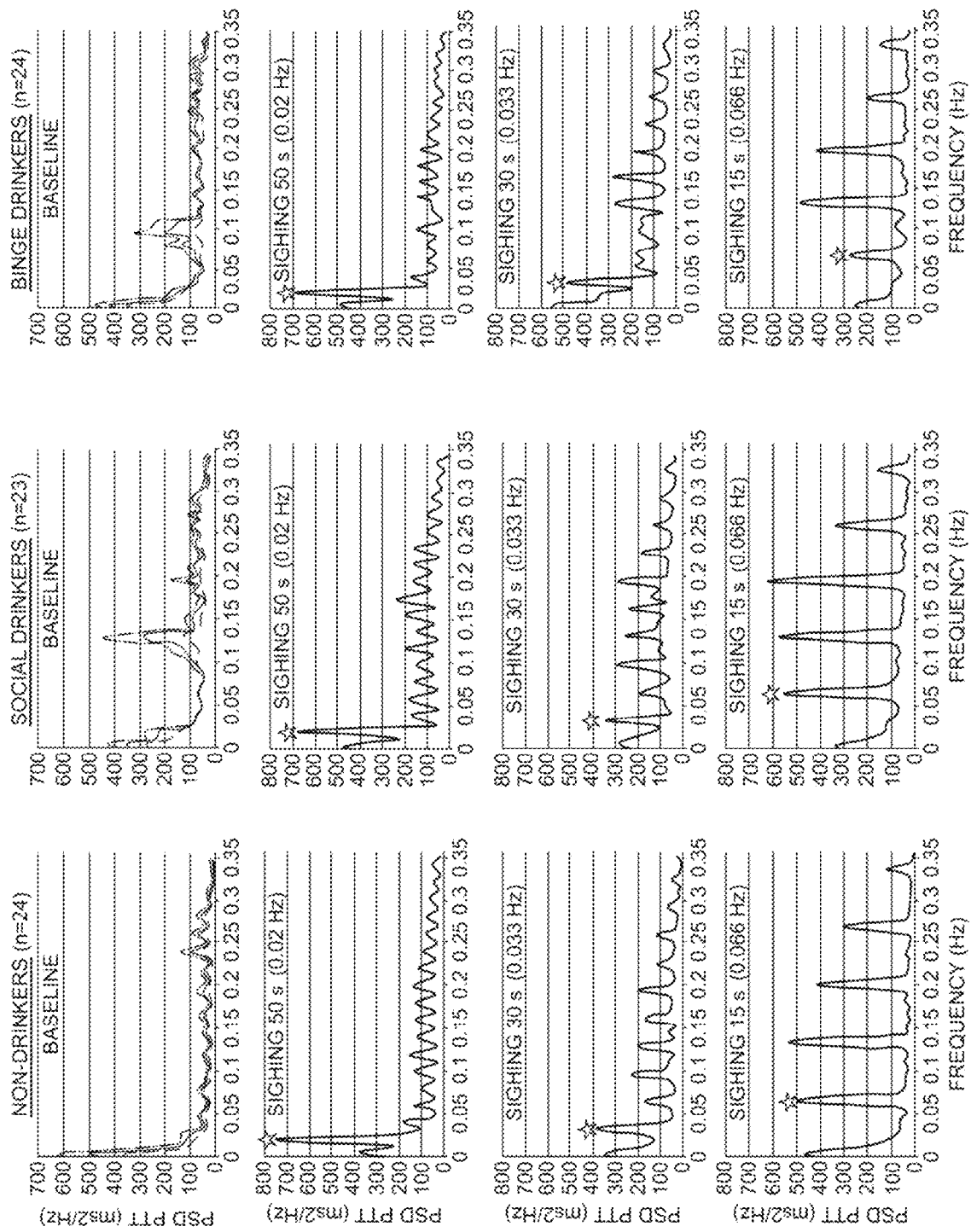

FIG. 3 provides graphs showing how the heart rate (RRI) and Vasomotor control systems reacted on paced sighing without habituation. FIG. 4 provides graphs showing high-amplitude oscillations at stimulation frequencies and at frequencies their harmonics were caused in HR and VT processes.

FIGS. 5A and 5C provide graphs showing that the magnitude of responses of the HR and VT control systems to the stimulation depended from the frequency of the paced sighing. FIGS. 5B and 5D provide graphs showing that the magnitude of responses of the HR and VT control systems to the stimulation depended on the participants' drinking behavior.

FIG. 5A shows that the average over three groups' responses of HR control system to the stimulation of various frequencies significantly differed. The response to 0.033 Hz sighing was significantly lower than 0.02 Hz and 0.066 Hz sighing. FIG. 5B shows that the average over each group responses to 0.02 to 0.033 Hz stimulation did not differ between groups while responses to 0.066 Hz stimulation was significantly lower in BD group than in SD and ND groups. The pattern of RRI response dependence from stimulation frequency had "V" shape in each group.

FIG. 5C shows the average over three groups' responses of VT control system to the stimulation of various frequencies significantly differed. The response to 0.033 Hz sighing was significantly lower than to 0.02 Hz sighing but did not differ from the response to 0.066 Hz sighing. FIG. 5D shows the average over each group VT responses were partly the same as HR responses to 0.02 and 0.033 Hz stimulation did not differ between groups while the response to 0.066 Hz stimulation was significantly lower in BD group than in SD and ND groups. The "V" shape pattern noted in HR control was absent in VT control since 0.066 Hz stimulation caused too low response in binge drinkers.

In order to explore the cardiovascular system, an applied engineering approach was used to evaluate heart rate (HR) and vascular tone (VT) reaction to various frequency sine-wave simulations. Paced sighing stimulation can cause large sine-wave oscillations HR and VT at the stimulation frequency and at array its harmonics. Due to the presence of harmonics rhythmical sighing, the tool gave the ability to examine the CVS in a wide frequency range. The significantly lower reaction of the HR control system on stimulation at 0.03 Hz than at 0.02 and 0.066 Hz gives reason to believe the frequency of 0.033 Hz is specific in the CVS control as well as the 0.1 Hz.

Significantly lower RRI and VT reactions in BD group than in SD and ND groups on stimulation at 0.066 Hz only prove that HR and VT control systems in BD group react on relatively slow changes in stimulus as well as in SD and ND groups but cannot properly react on more fast changes in stimulus. This suggests that the plasticity of the CVS control systems was considerably reduced in participants who drank at least 4-5 drinks within 2 hours at least 5 times per month. A 5-minute 0.066 Hz paced sighing with RRI registration can be used to evaluate disorders in cardiovascular systems in binge drinkers.

Example 2

The study was sought to examine cardiovascular regulation and coupling in young adult (18 to 25 years of age) BDs compared to that in young adult ND and SD. A broad perspective on the cardiovascular system was taken by simultaneously and non-invasively measuring multiple cardiovascular reactions at rest and during two tasks that provoked either sympathetic (paced sighing at 0.03 Hz, or 2 sighs per minute) or parasympathetic (paced breathing at 0.1 Hz, or 6 breaths per minutes) activity. The goal was to characterize early signs of cardiovascular change in individual cardiovascular parameters (i.e., average and variability in heart rate, stroke volume, vascular tone, and blood pressure), relationship of these parameters to blood pressure control (i.e., via respective baroreflex branches), and the coupling of the parameters (i.e., to characterize the coordination between cardiovascular functions). Assessment of whether changes appeared cumulative as drinking histories lengthened was also explored. Binge drinking was broadly hypothesized to exert subtle but cumulative adverse effects on the cardiovascular system based on evidence from the effects of acute alcohol intoxication on the cardiovascular system and evidence of adverse effects of long-term chronic alcohol use on overall cardiovascular health.

1. Method 1.1. Participants

Seventy-one college student volunteers (36 women) were enrolled in the study (21.9 (SD: 2.15) years old, range 18-25). Exclusion criteria were the current use of medication affecting the cardiovascular system, a history of cardiac abnormality, high blood pressure (>140/90 mmHg), any medical condition that can directly or indirectly influence the vascular tone or cardiovascular functioning, or a body mass index indicative of obesity. Individuals with past year treatment for any psychiatric disorder were also excluded, as well as individuals who reported nicotine product use in the prior 3 months, regular (monthly) use of psychoactive substances (other than alcohol), or who had a lifetime diagnosis of a substance use disorder. For women, pregnancy and lactation were additional exclusion criteria.

Participants were recruited through the university and community bulletin boards, electronic postings, and flyers. The racial composition was: White (60.5%), Asian (22.5%), Black or African American (11.3%), and mixed or other (5.7%); 16.9% self-reported being Hispanic or Latino. The participants, males and females, were grouped based on drinking profiles: (a) NDs who consumed no alcohol in the past 3 months, and consumed no more than 2 drinks per occasion, with less than 4 occasions per year (n=24), (b) SDs who drank no more than 2 (women) or 3 (men) drinks per occasion but self-reported drinking at least 2 times per month (n=23), and (c) BDs who drank at least 4 (women) or 5 (men) drinks within ~2 hours (thus achieving a blood alcohol concentration of ~0.08%) at least 5 times per month (n=24).

1.2. Procedure

An initial telephone screening interview was conducted to assess eligibility for study inclusion. Upon arrival at the laboratory, all eligible participants provided written informed consent and were compensated for their time. Each participant completed one laboratory session that lasted approximately 2 hours and started between 10 a.m. and 2 p.m. to minimize biological circadian variations. After completion of a series of questionnaires, participants were seated in a comfortable chair located 2.5 m in front of a large TV screen in a sound attenuated, dimly lit room. ECG, beat-to-beat blood pressure, and thoracic respiration were continuously collected while participants completed five 5-minute tasks (baseline 'Vanilla' task, 3 paced sighing tasks at 0.02, 0.033, and 0.066 Hz, and a paced breathing task at 0.1 Hz). This study focuses on the comparison of baseline, 0.033 Hz sighing (sympathetic challenge), and 0.1 Hz breathing (parasympathetic challenge).

1.3. Self-Report Questionnaires

Participants provided self-report information during the initial telephone screening interview that was reviewed upon arrival at the laboratory. Gender and date of birth from this screening was used in the present study. Participants then completed several surveys, including a 15-item alcohol use questionnaire that asked about the age of first drink, alcohol preferences, recency of last drink, and the frequency and quantity of alcohol use over the past week, past month, and past year. A single variable that estimated the duration of alcohol use was computed by subtracting current age from the age of first drink.

1.4. Physiological Tasks

The first task was a low-demand cognitive task that provides a more standardized baseline than an uncontrolled resting state. A rectangle presented in the center of the TV screen changed color every 10 sec for 5 min, and participants were asked to silently count the number of blue rectangles. This task served as the BaseLine ("BL") task and was also completed first.

Three Paced Sighing ("PS") tasks were then completed in counterbalanced order. In these tasks, participants voluntarily sighed when the TV screen turned red; between sighs, participants breathed normally. Participants were instructed to inhale fully and quickly by mouth, but not too deeply, and exhale in a relaxed way. Before recording, participants underwent a short training to become familiarized with the sighing pattern. The red screen presentation was programmed using E-Prime software (Psychology Software Tools, Inc., Pittsburgh, Pa.) with an accuracy of ±1 ms. Three pacing frequencies were used in the overall study design: 0.02 Hz (one sigh per 50 sec), 0.033 Hz (one sigh per 30 sec), and 0.066 Hz (one sigh per 15 sec). For this study, paced sighing at 0.033 Hz was used as a sympathetic challenge (i.e., elicits a robust response from the sympathetic nervous system).

A single Paced Breathing ("PB") task involved breathing at a rate of six breathing cycles per minute (0.1 Hz) by following a visual pacer (e.g., Easy Air, Biofeedback Foundation of Europe, Montreal, Canada) presented on the TV screen. This pace is much slower than normal breathing (12-20 breathes per minute). Before recording, participants underwent a short training to ensure that they breathed slowly, but not too deeply to avoid possible hyperventilation. This task is well-established to elicit a vagal response and synchronize neurocardiac signaling with respiratory sinus arrhythmia. It was used as a parasympathetic challenge.

1.5. Physiological Assessment

A PowerLab Acquisition System (e.g., ADInstruments, Colorado Springs, Colo.) and Finometer MIDI (e.g., Finapres, Amsterdam) was used to collect electrocardiogram (ECG), beat-to-beat blood pressure, and thoracic respiration. The sampling rate for all data collection was 2000 Hz. A standard lead II was used for ECG measurement. A cuff-sensor for blood pressure beat-to-beat continuing measurement was attached to the second phalange of the right middle finger. Respiratory data were collected from a belt containing transducers that were set around the upper part of the chest, just below the underarms. Respiration was calibrated before the start of physiological records using a standard 800 ml bag into which participants were asked to breathe in and out five times. Physiological data were collected during all tasks.

1.6. Analysis of Physiological Data

Recorded physiological data was exported to a software application (e.g., WinCPRS software available from Absolute Aliens Oy, Turku, Finland) to measure heart beat-to-beat time intervals (R-to-R wave intervals of ECG; RRI), systolic and diastolic arterial blood pressure (SAP and DAP), stroke volume, and pulse transit time. SAP and DAP were measured as the peak and valley, respectively, of each finger pulse recorded by the Finometer MIDI. The ModelFlow methodology for cardiac output measurement was used to measure beat-to-beat stroke volume from the same finger pulse. Pulse transit time for each heartbeat was measured as a time interval between the R-spike of the ECG and the peak of the corresponding finger pulse recorded by the Finometer MIDI and was used as a proxy measure of VT. Higher pulse transit time corresponds to lower vascular tone. Beat-to-beat data was transformed into an equidistant waveform through cubic interpolation and 4 Hz resampling.

Mean RRI, stroke volume, pulse transit time, and SAP were calculated for each task. Heart Rate Variability ("HRV") was measured in the time domain as the root of the mean squared differences of successive intervals ("RMSSD"), which provides a gauge of parasympathetic activity. HRV was also calculated after Fourier transformation as total power of the RRI spectrum in frequency range of (Total HRV, 0.001-0.05 Hz) and as spectral power in the high (HF HRV, 0.15-0.5 Hz) and low (LF HRV, 0.05-0.15 Hz) frequency ranges of the RRI spectrum. HF HRV serves as a measure of parasympathetic influence on heart control, whereas LF HRV is a composite index thought to reflect elements of baroreflex, vascular, sympathetic and parasympathetic activity. To further characterize physiological mechanisms underlying resting state LF HRV, the power peaks were assessed in the LF range of the baseline RRI spectra for each participant. Three power peaks were identified that could potentially differentiate control of heart rate from the control of vascular tone. The power peak at ~0.1 Hz was used to assess control of heart rate; the 0.066 Hz and ~0.08 Hz power peaks were used to capture control of vascular tone.

Heart rate, stroke volume, and vascular tone baroreflex gains were calculated to capture the sensitivity of system elements to changes in blood pressure. Using cross-spectral analysis of simultaneously recorded beat-to-beat RRI, stroke volume, pulse transit time, and systolic arterial pressure ("SAP"), transfer functions with SAP as the input and RRI, stroke volume, or pulse transit time as the outputs (SAP-RRI, SAP-SV, and SAP-PTT transfer functions, respectively) were calculated. HR, SV, and VT baroreflex gains (HR BRS, SV BRS, and VT BRS gains) were estimated as the average value of corresponding transfer function in the low-frequency range (0.05-0.15 Hz), where coherence between SAP and RRI, stroke volume, or pulse transit time was >0.5. Thus, baroreflex gain was estimated as the magnitude of change in RRI (ms), stroke volume (ml), and pulse transit time (ms) in response to one unit of change in systolic arterial pressure (mmHg).

1.7. Statistical Analysis

Initial analyses compared the BD, SD, and ND groups using repeated measures analysis of variance (e.g., using SAS 9.3, SAS Institute, Cary, N.C.). There were no significant differences between the ND and SD groups in any average and variability measures from any physiological domain. Subsequent analyses focused only on differences between the SD and BD groups.

Repeated measures analysis of variance was used to calculate SD and BD group differences in mean HR, SV, SAP, and PTT; multiple measures of HRV; and gain in the HR, SV, and VT baroreflex branches. Linear regression was used to assess the relationship between the duration of alcohol use and changes in baroreflex gain and the power peaks in baseline RRI spectra at frequencies of 0.066, 0.08, and 0.1 Hz. Finally, the pattern of correlations between average HR, SV, PTT, and SAP was plotted by the group for each task to descriptively characterize the interrelation of cardiovascular functions at rest and in response to challenge. Repeated measures ANOVA was used to calculate group differences in mean HR, stroke volume, SAP, and pulse transit time, multiple measures of HRV, and gain in the HR, stroke volume, and vascular tone baroreflex branches. A Bonferroni correction for multiple testing was used. Based on performing 10 repeated measures ANOVAs, alpha was set at p<0.005.

Specifically, within the BD group, linear regression was used to assess the relationship of years of alcohol use to vascular tone baroreflex gain and to power in LF spectral peaks in baseline RRI spectra. Years of alcohol use was estimated by subtracting current age from the age of first drinking episode. Cardiovascular parameters were log transformed prior to repeated measures ANOVA and linear regression analysis. Normalized baseline RRI spectra were used in the latter analyses. Regression analysis also was used to describe the pattern of relationships between cardiovascular parameters. The coefficient of determination (R2) was computed between average HR, stroke volume, pulse transit time, and SAP for each task in each group (ND, SD, BD), and significant R2 were plotted.

2. Results

Mean Cardiovascular Reactions.

Figure 11:
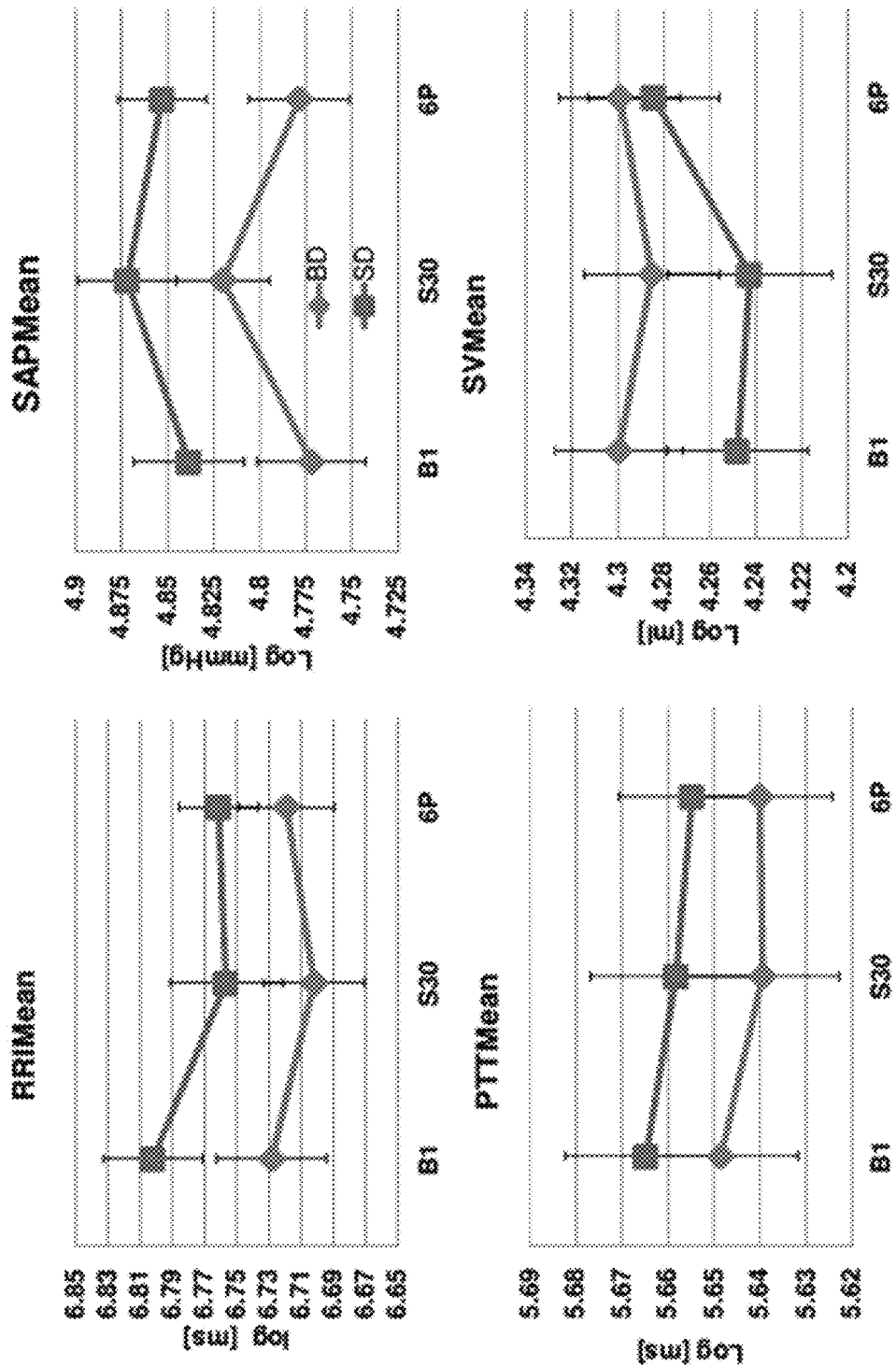
FIG. 11 shows mean values of the cardiovascular parameters for a BD group and a SD group in three tasks, including rest state (B1) during paced sighing at 0.033 Hz (S30) and during paced 6 times per minute breathing (6P).

Mean RRI showed a significant task (BL, PS, PB) effect ($F_{2,90}=8.78$, $p<0.05$), but non-significant group (SD vs BD) and task x group effects. Mean RRI during baseline was significantly higher than mean RRI during PS ($F_{1,45}=24.4$, $p<0.05$) and PB ($F_{1,45}=6.4$, $p<0.05$), but differences between PS and PB were non-significant (FIG. 11). Mean stroke volume showed a significant task effect on mean stroke volume ($F_{2,90}=3.31$, $p<0.05$), but no group effect or task x group interaction. The only significant difference was between PB and PS ($F_{1,45}=5.99$, $p<0.05$; FIG. 11). Mean SAP showed a significant task effect ($F_{2,90}=10.14$, $p<0.05$), but no group effect or task x group interaction. Mean SAP during PS was significantly higher than during BL ($F_{1,45}=29.52$, $p<0.05$) and PB ($F_{1,45}=10.68$, $p<0.05$; FIG. 11). There were no significant differences detected in mean pulse transit time (FIG. 11).

Figure 6:
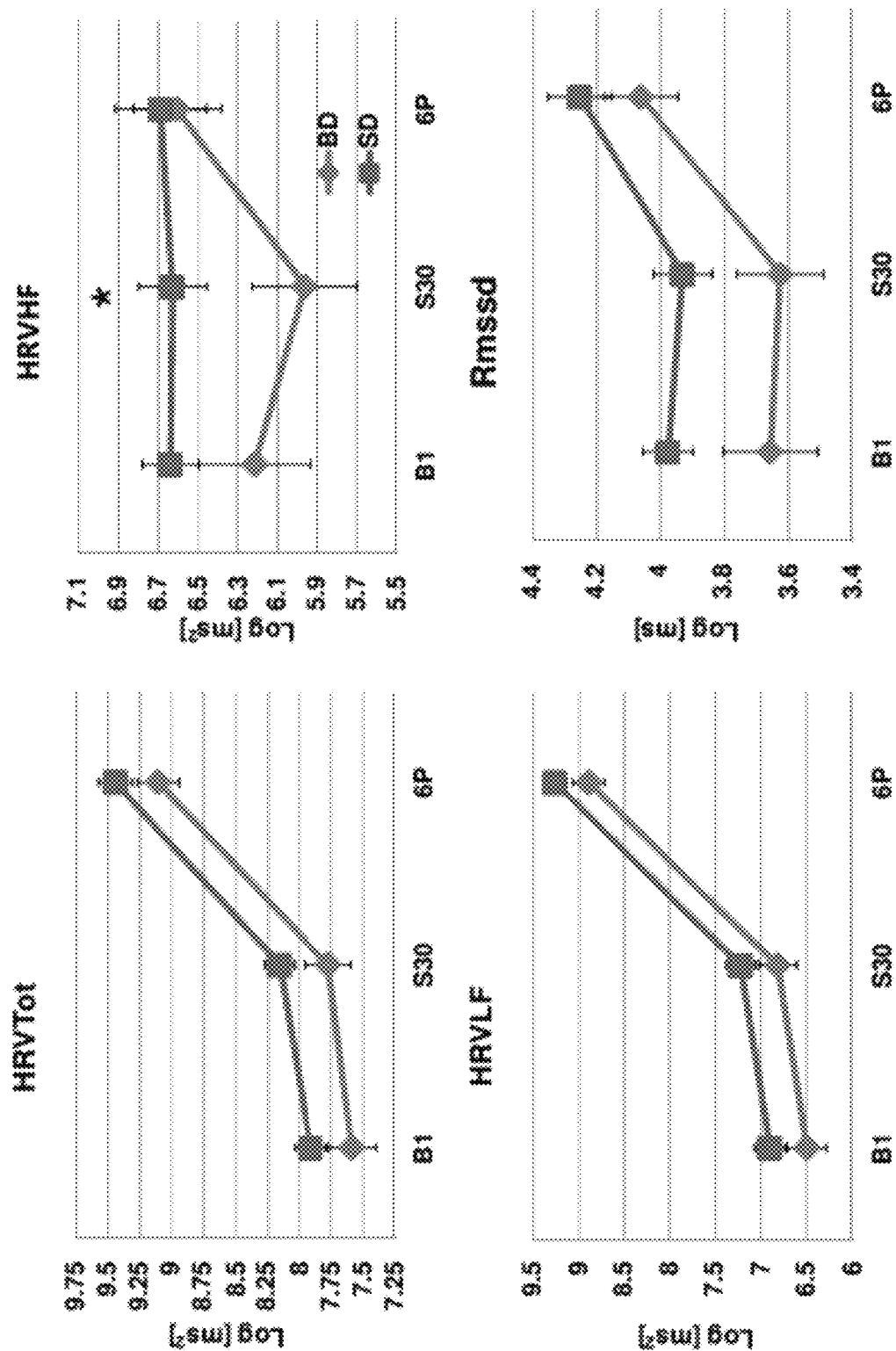
FIG. 6 shows between-group comparisons of HRV indices (HRVTot, HRVHF, HRVLF, and RMSSD) in three tasks, including rest state (B1) during paced sighing at 0.033 Hz (S30) and during paced 6 times per minute breathing (6P).

Similar to the mean cardiovascular parameters, measures of HRV showed significant task effects, but no significant group or group x task effects. There also was a significant effect of task on HRV, but no significant group differences or group x task interactions (see the below TABLE 1 and FIG. 6). The paced sighing task significantly increased LF HRV compared to baseline, and the paced breathing task increased LF HRV and RMSSD compared to baseline.

TABLE 1

Repeated Measures ANOVA and Univariate Planned Contrasts for t RMSSD, HRVHF, HRVLF, and LHRVTot: BD vs. SD

| Overall effect | LRmssd | | | LHRVHF | | | LHRVLF | | | LHRVTot | | |
|---|---|---|---|---|---|---|---|---|---|---|---|---|
| | df | F | $\eta_p^2$ | df | F | $\eta_p^2$ | df | F | $\eta_p^2$ | df | F | $\eta_p^2$ |
| Stimulus effects | 2.90 | 45.32*** | | 2.90 | 4.28* | | 2.66 | 239*** | | 2.90 | 189*** | |
| B1 vs. S30 | 1.45 | 1.09 | | 1.45 | 2.04 | | 1.45 | 9.10** | | 1.45 | 8.39** | |
| B1 vs. 6P | 1.45 | 42.14*** | | 1.45 | 1.97 | | 1.45 | 284*** | | 1.45 | 217*** | |
| S30 vs. 6P | 1.45 | 85.43*** | | 1.45 | 10.9** | | 1.45 | 400*** | | 1.45 | 319*** | |
| Group effects | 1.45 | 3.07 | 0.07 | 1.45 | 1.86 | 0.03 | 1.45 | 3.36 | 0.07 | 1.45 | 3.14 | 0.07 |
| Within-subjects x Between-subjects interaction effects | | | | | | | | | | | | |
| Stimulus x Group | 2.90 | 1.26 | 0.02 | 2.90 | 2.79 | | 2.90 | 0.02 | 0.0 | 2.90 | 0.05 | 0.0 |
| Group effects on each stimulus | | | | | | | | | | | | |
| B1: BD vs. SD. | 1.45 | 3.54 | 0.07 | 1.45 | 1.75 | 0.04 | 1.45 | 2.10 | 0.04 | 1.45 | 2.09 | 0.04 |
| Sigh 30: BD vs. SD | 1.45 | 3.37 | 0.07 | 1.45 | 4.35* | 0.09 | 1.45 | 2.45 | 0.05 | 1.45 | 3.01 | 0.06 |
| 6P: BD vs. SD | 1.45 | 1.56 | 0.03 | 1.45 | 0.07 | 0.00 | 1.45 | 2.80 | 0.06 | 1.45 | 2.51 | 0.05 |

Figure 7:
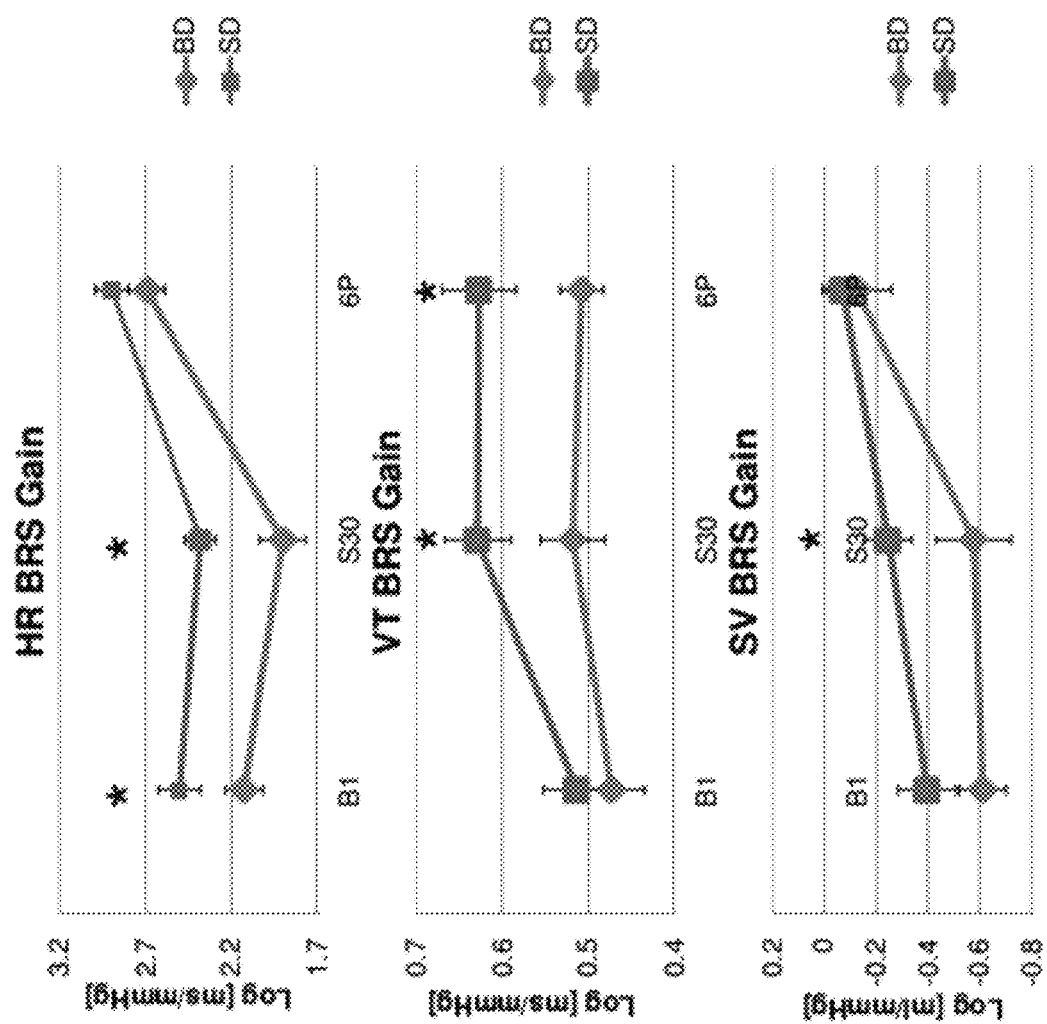
FIG. 7 shows between-group comparisons of the HR, VT and SV baroreflex gains in three tasks, including rest state (B1) during paced sighing at 0.033 Hz (S30) and during paced 6 times per minute breathing (6P).

There was a significant task effect for all three baroreflex gain measures and a significant group effect for HR baroreflex gain and VT baroreflex gain (TABLE 2 and FIG. 7). Post-hoc analyses revealed that the paced sighing task significantly increased gain the VT branch and decreased gain the HR branch compared to baseline. The paced breathing task significantly increased all three BRS gains compared to baseline. There were no significant group x task interactions.

TABLE 2

Repeated Measures ANOVA and Univariate Planned Contrasts for the HR, VT, and SV BRS Gains: BD vs. SD

| | Contrast | | | | | | | | |
|---|---|---|---|---|---|---|---|---|---|
| | HR BRS Gain | | | VT BRS Gain | | | SV BRS Gain | | |
| Overall effect | df | F or t | $\eta_p^2$ | df | F or t | $\eta_p^2$ | df | F or t | $\eta_p^2$ |
| Stimulus effects | 2.90 | 50.42*** | 0.24 | 2.90 | 6.22** | 0.07 | 2.66 | 8.57*** | 0.05 |
| B1 vs. S30 | 1.45 | 7.26** | | 1.45 | 8.14** | | 1.45 | 0.16 | |
| Bi vs. 6P | 1.45 | 45.27*** | | 1.45 | 8.64** | | 1.45 | 9.59** | |
| S30 vs. 6P | 1.45 | 92.91*** | | 1.45 | 0.07 | | 1.45 | 19.73*** | |
| Group effects | 1.45 | 6.96* | 0.14 | 1.45 | 4.14* | 0.09 | 1.45 | 2.73 | 0.05 |
| Within-subjects × Between-subjects interaction effects | | | | | | | | | |
| Stimulus × Group | 2.90 | 1.66 | 0.09 | 2.90 | 1.51 | 0.08 | 2.78 | 1.20 | 0.02 |
| Group effects on each stimulus type: | | | | | | | | | |
| B1: BD vs. SD. | 1.45 | 5.57* | 0.11 | 1.45 | 0.54 | 0.01 | 1.45 | 0.66 | 0.01 |
| Sigh 30: BD vs. SD | 1.45 | 8.95** | 0.16 | 1.45 | 4.20* | 0.08 | 1.45 | 4.75* | 0.09 |
| 6P: BD vs. SD | 1.45 | 2.01 | 0.04 | 1.45 | 5.78* | 0.11 | 1.45 | 0.07 | 0.00 |

Figure 8:
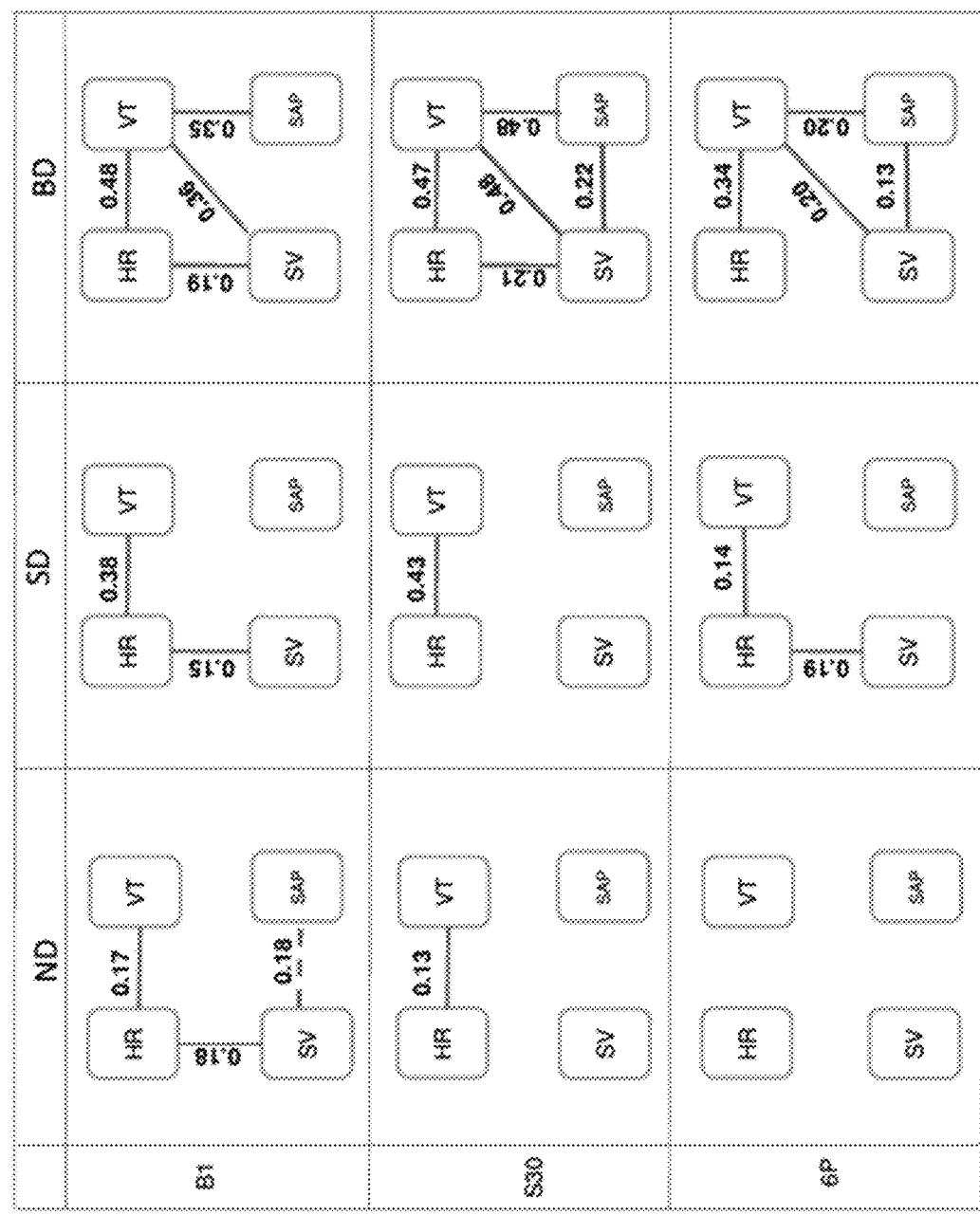
FIG. 8 shows patterns of interrelations between mean HR, SV, SAP, and PTT during a simulation.

The pattern of interrelations between mean HR, SV, SAP, and PTT changed only a little under stimulation conditions (S30 and 6P tasks versus B1 task) but were significantly different between groups (FIG. 8). The structures/patterns in ND and SD group had small distinctions, but in BD and SD groups they were crucially different in all three tasks. The number of the interrelation pairs of the mean parameters and the strength of their links were higher in BD group than in SD or ND group.

In the B1 task, the association between mean values of HR and VT was observed in all 3 groups. Higher VT corresponded to higher HR. Association strength was higher in groups where participants drank more (adjusted $R^2$ was 0.17 in ND group, 0.38 in SD, and 0.48 in BD group). Association strengths between HR and SV in ND, SD, and BD groups were almost equal. BD group disclosed three positive associations: SV×VT, SAP×VT, and SV×SAP, which were absent in SD and ND group. In the S30 task, which activates the sympathetic control of the CVS, HR×VT association remained the same in all three groups, as it was in the B1 task. Unlike the B1 task, the structure/pattern of HR×SV associations in the S30 task disappeared in ND and SD groups, but a new SV×SAP association appeared in BD group. In the 6P task, which activates the parasympathetic control of the CVS, all associations disappeared in ND group. In SD group, the HR×VT association remained, but with considerably lower power; the HR×SV association, lost in the S30 task, came back to the structure/pattern. In BD group, the structure/pattern was almost the same as in S30 task, but there was no HR×SV association, all other associations had considerably lower power than in B1 and S30 tasks.

Figure 9:
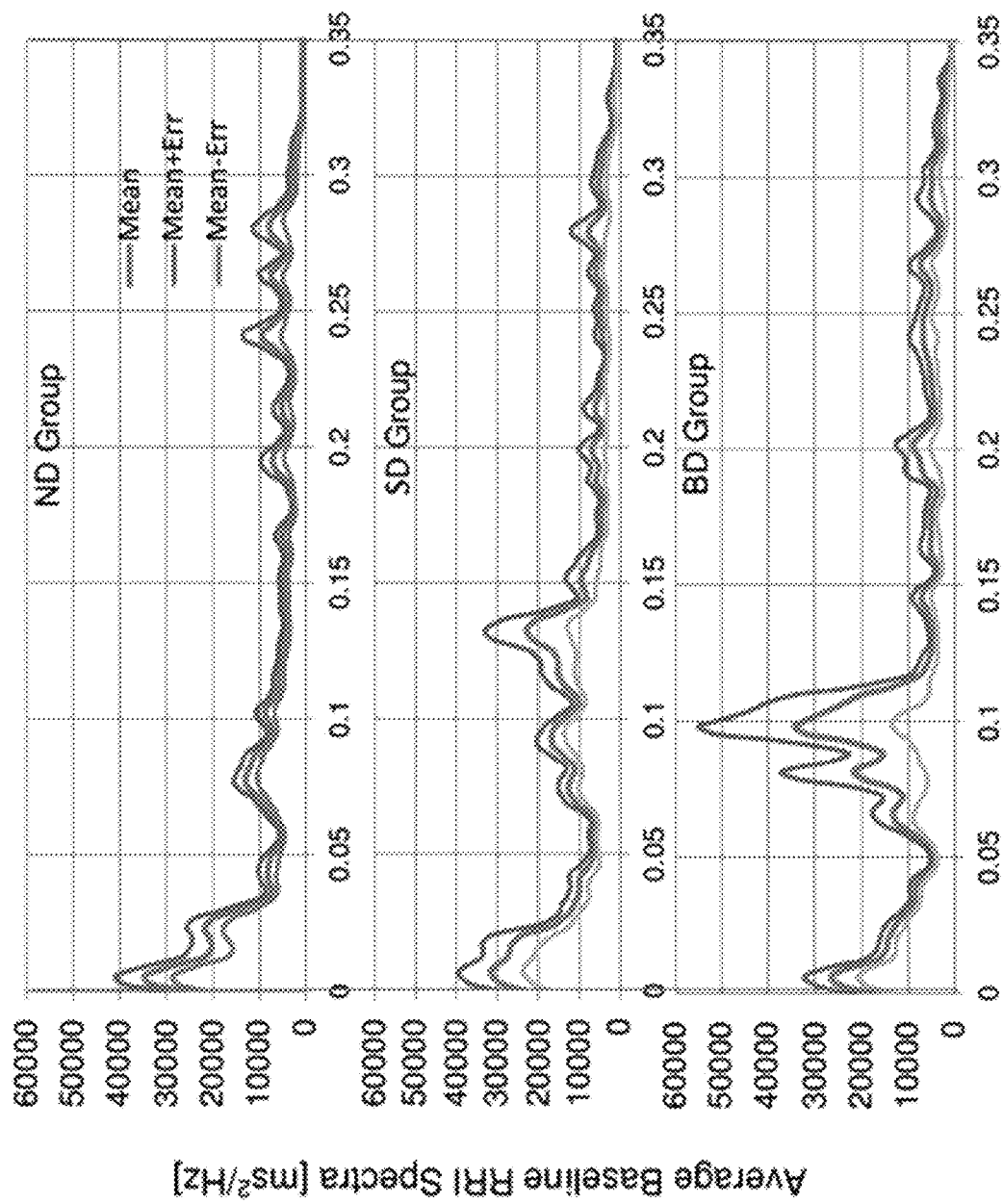
FIG. 9 shows a baseline RRI frequency spectra averaged across participants in ND, SD, and BD groups.
Figure 10:
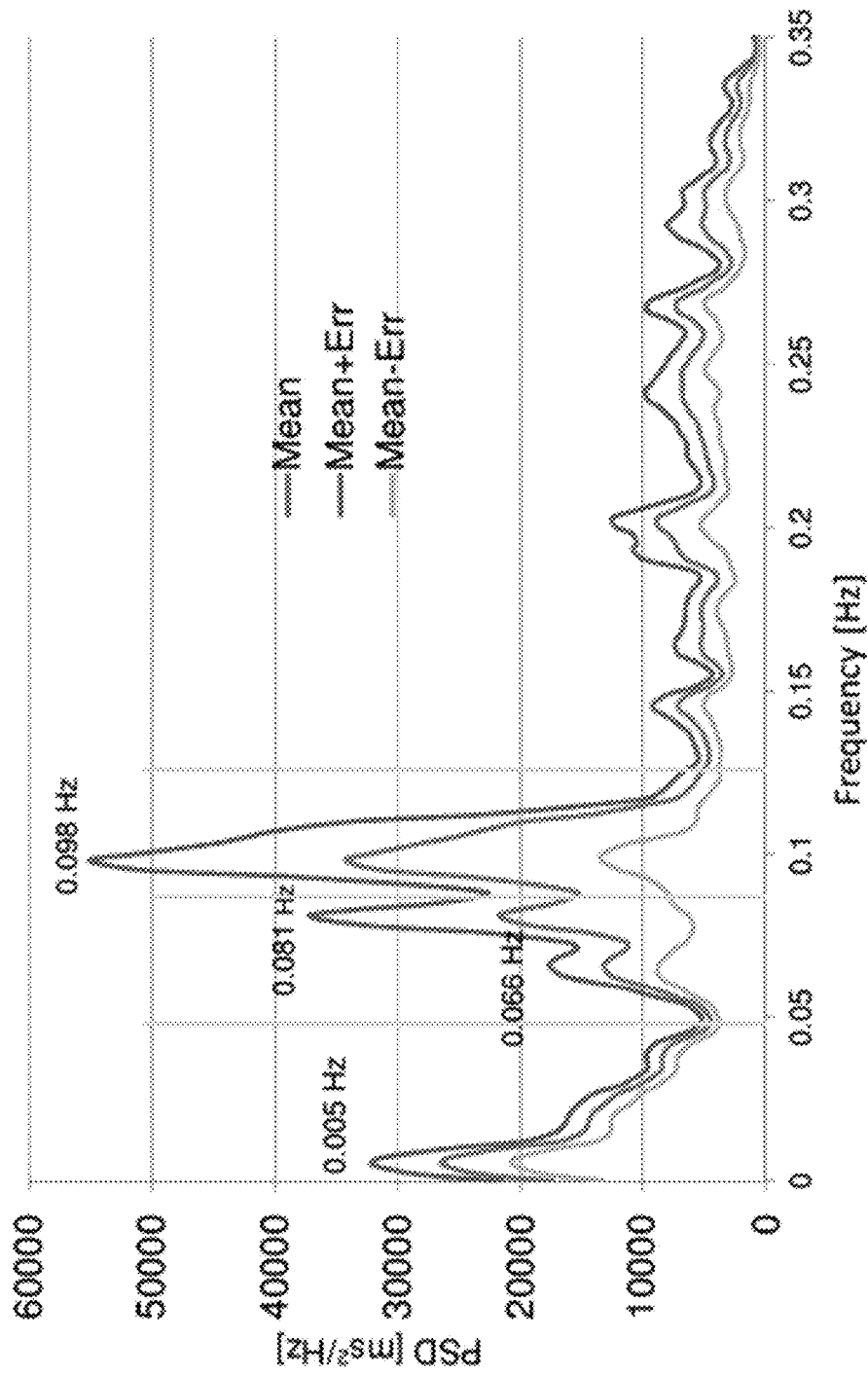
FIG. 10 shows an averaged baseline RRI spectrum for a BD group where the low-frequency range is divided into two functionally different parts.

Between-Group Comparison of RRI Frequency Spectra Averaged Across Participants in BD, SD, and ND Groups Baseline RRI frequency spectra averaged across participants in BD, SD, and ND groups presented in FIG. 9, depict extensive group-differences. Overall, the structures/patterns of the spectra in the groups are the same. The very low-frequency range (0.001-0.05 Hz) of the spectra in all three groups has an explicit peak at a frequency about 0.005 Hz and a valley around 0.05 Hz. In the low (0.05-0.15 Hz) and high (0.15-0.5 Hz) frequency ranges the spectra have several peaks. Substantial group-differences are revealed in the peaks distribution in the low-frequency range. Thus, spectra of all three groups included explicit peaks at frequencies of about 0.08 Hz and 0.1 Hz. Additionally, BD group spectra had peaks at ~0.066 Hz and ~0.15 Hz, while SD group at 0.132 Hz and ~0.15 Hz (see below Table 3). The mean and particularly standard deviation values of the peaks in BD group's spectrum were considerably higher than in SD or ND group's spectra. In all groups, the power of the spectra in high-frequency range was less than in low-frequency range, relatively stable in the range of 0.15-0.3 Hz, and reduced at a frequency higher than 0.3 Hz. FIG. 10 presents an averaged baseline RRI spectrum for a BD group where the low-frequency range is divided into two functionally different parts.

TABLE 3

Power peaks in averaged baseline RRI spectra

| Alcohol Group | Frequency of power peaks in averaged baseline RRI spectra in ND, SF, and BD groups | | | | |
|---|---|---|---|---|---|
| | Hz | Hz | Hz | Hz | Hz |
| ND | | 0.078 | 0.1 | | |
| SD | | 0.076 | 0.093 | 0.132 | 0.15 |
| BD | 0.066 | 0.081 | 0.098 | | 0.144 |

Figure 12A:
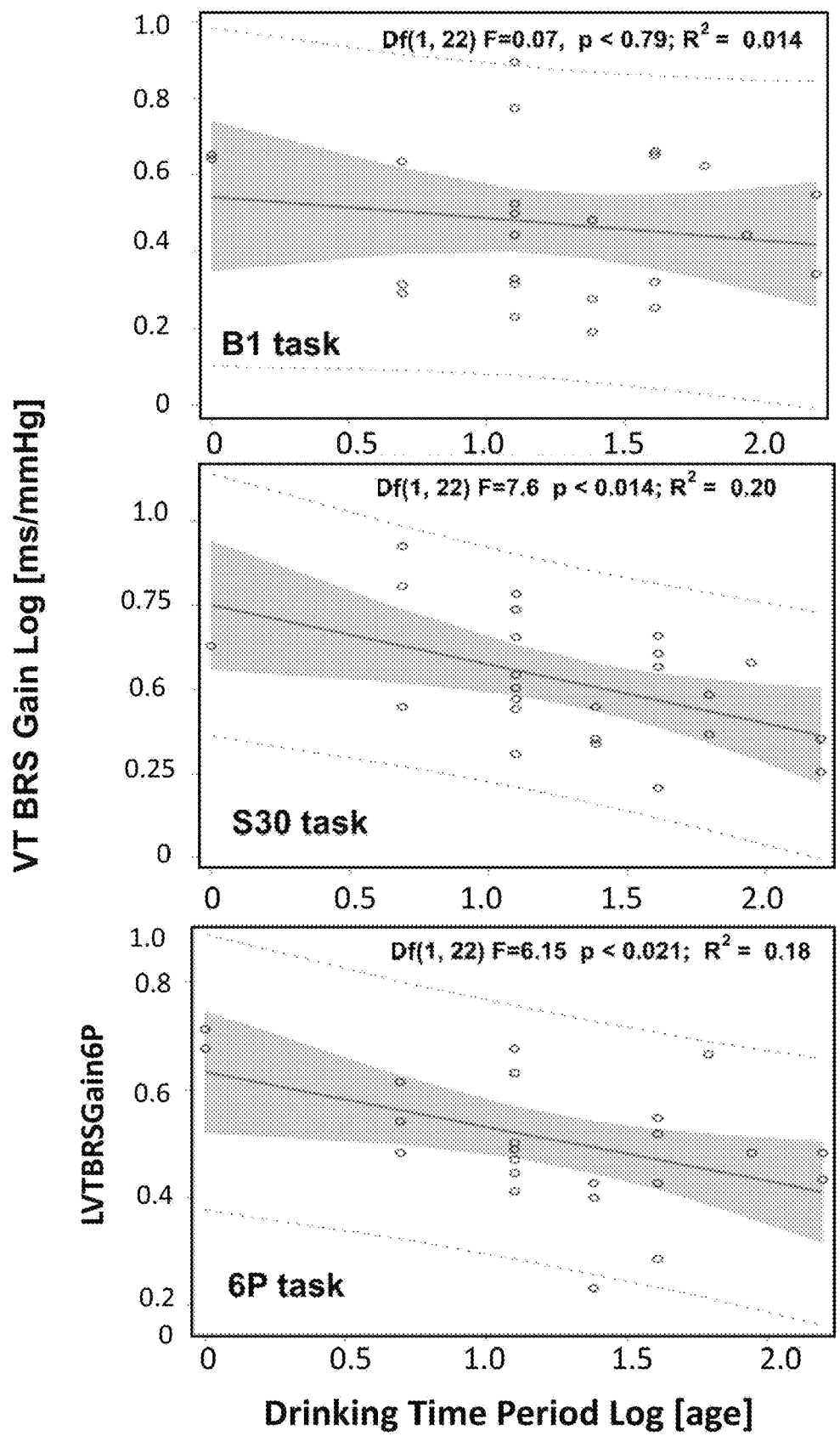
FIGS. 12A and 12B (collectively "FIG. 12") show association of vascular tone baroreflex gain (VT BRS Gain) (FIG. 12A) in a BD group with drinking time period and association of 0.066, 0.081, and 0.098 Hz peaks amplitude in a BD group with drinking time period (FIG. 12B).
Figure 12B:
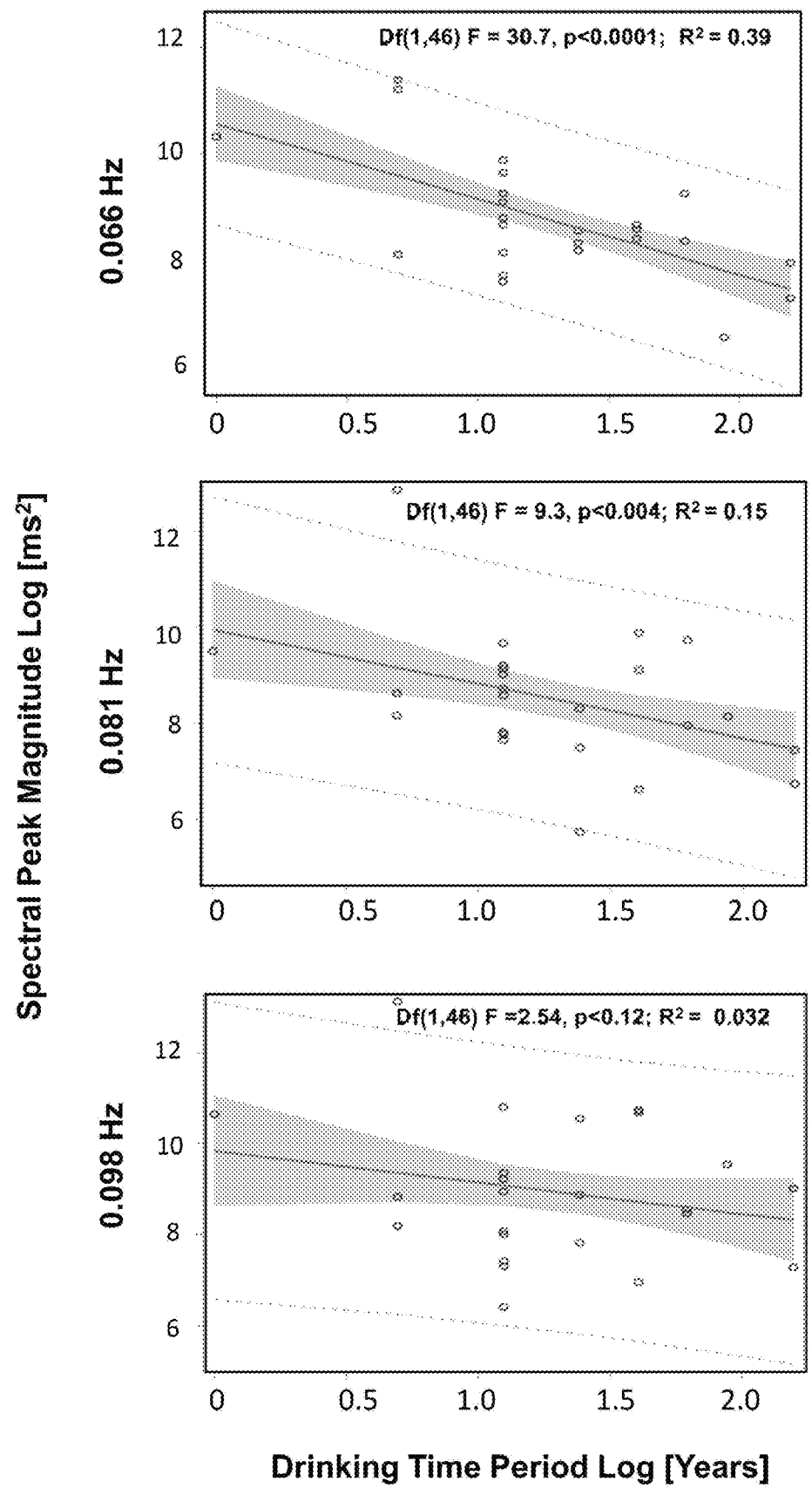

Value of Some Cardiovascular Parameters in Binge Drinkers Associated with their Drinking Time Period Results of the regression analysis revealed significant negative associations between values of participants' time period of drinking in BD group and their VT BRS Gains. These associations were revealed in S30 and 6P tasks (FIG. 12A) where VT BRS Gain in BD group was significantly lower than in SD group (FIG. 7). However, such association was absent in B1 task (FIG. 12A) where VT BRS Gain in BD and SD groups was equal (FIG. 7). A significant negative association was also revealed in BD group between the time period of participants' drinking and the magnitude of power peaks at 0.066 Hz and 0.081 Hz in B1 RRI spectra, but there was no association between the time period of drinking and the power peak at 0.098 Hz (FIG. 12B).

As discussed above, comprehensive sets of cardiovascular parameters were collected in three groups of young healthy binge and social alcohol drinkers and non-drinkers and compared between groups in order to find early signs of cardiovascular dysregulation in binge drinkers. The parameters were measured at baseline state and during two tasks that either enhance sympathetic (S30 task) or parasympathetic (6P task) control of the cardiovascular system (CVS) to simulate daily ordinary life situations.

The common cardiovascular parameters: mean HR, BP, VT, SV and HRV indices—did not differ significantly between the three groups. Significant group differences were found in: the values of HR BRS, VT BRS, and SV BRS Gains; the reactions of cardiovascular parameters to paced sighing (S30) and paced breathing (6P) stimulation tasks; and the correlation structures of interrelations between HRMean, VTMean, SVMean, and SAPMean.

Between-Group Comparison of the HR, VT, and SV BRS Gains

As known, heavy alcohol consumption depresses the baroreflex. It was found that all three baroreflex indices (HR BRS, VT BRS, and SV BRS Gains) did not differ between ND and SD drinkers groups but were significantly lower in BD than in SD group (FIG. 3B and Table 2). It was also found that S30 task augmented only VT BRS Gain, while 6P task activated all three BRS branches (FIG. 7 and TABLE 2 provided above), and that during S30 and 6P tasks, VT BRS Gain in BD group was significantly negatively associated with the binge drinking time period (FIG. 12A). Longer binge drinking experience caused a higher reduction in VT BRS Gain, i.e., regular extensive drinking cumulatively affected vascular tone regulation. This correlation became active when autonomic control of the CVS was strengthened by stimulation tasks. In contrary, there were no correlations of HR BRS or SV BRS Gains with the duration of binge drinking experience.

These findings allow for the hypothesis that effect of alcohol on vessels endothelium could be the key origin for cardiovascular problems caused by alcohol consumption.

The decrease in all three BRS Gains in binge drinkers group might be explained by declining sensitivity of the baroreceptors located in the walls of the arteries. Endothelial dysfunction caused by persistent alcohol consumption decreases the sensitivity of the baroreceptors and consequently reduces the activity of all baroreflex branches.

The baroreflex is an essential reflex that is responsible not only for regulation of cardiovascular processes, but also for the continual, bidirectional communication between the heart and brain, which provides optimal inhibitory modulation of the brain through afferent fire from baroreceptors to support regulation of emotions, stress, and behavior, and allows the individual to precisely adapt to changes in his/her internal milieu and external environment by integrating neural and cardiovascular reactions. Therefore, reduction in BRS activity in young healthy binge drinkers can be considered as a meaningful early negative sign for general health and, in particular, reduction in VT BRS Gain as an early prognostic sign for future cardiovascular disorders.

Between-Group Comparison of Sympathetic and Vagal Tone

To evaluate the sympathovagal balance, HRV indices and mean values of cardiovascular functions were applied. Although binge drinking did not change the HRV indices significantly, the RMSSD and HRVHF indices responsible for activity evaluation of parasympathetic nervous system tended to be lower in BD group than in SD group (FIG. 12B), i.e., the vagal tone tended to be lower in binge than in social drinkers. Mean values of the cardiovascular parameters did not differ significantly between BD and SD groups, but mean values of the HR, VT, and SV tended to be higher in BD group than in SD group (FIG. 11). This suggests that the sympathetic tone tended to be higher in BD group than in SD group. Thus, there was found to be a tendency to shift the sympathovagal balance in binge drinkers toward the sympathetic side.

Between-Group Comparison of the Correlation Structures of Interrelations Between Mean Values of the Cardiovascular Functions Overall, the mean values of the cardiovascular functions reflect metabolic state of the body. Although the mean values of the cardiovascular parameters did not have significant differences between groups, the correlation structures of their interrelations in ND and BD groups and in SD and BD groups were crucially different. There were small differences between ND and SD groups (FIG. 8). The number of the interrelation pairs of mean parameters and the strength of their links were higher in BD group than in SD or ND groups. A hypothesis was made that this finding can be interpreted as an adaptive compensatory change on the cardiovascular regulation in response to the reduction in baroreflex activity and strengthened sympathetic tone in binge drinkers. Usually, the baroreflex system provides interconnection between cardiovascular functions which, in particular, efficiently support the regulation of metabolic needs for cognition, emotions, and stress. This is a dynamic regulation process based on functions variability. It seems the reduction in BRS gains and shift of sympathovagal balance towards the sympathetic side in binge drinkers call for additional metabolic control of the cardiovascular functions at the level of their mean values as a higher level than the level of functions variability. The fact the S30 task strengthened the power of correlations while 6P task decreased it (FIG. 8) confirms the idea that the shift of sympathovagal balance affected the correlation structures of mean values in cardiovascular functions. A distinctive hallmark of the correlation structures in BD group was the presence of SV×VT and SAP×VT correlation pairs that were absent in ND and SD group structures.

Between-Group Comparison of Baseline RRI Frequency Spectra Averaged Across Participants in Binge, Social and Non-Drinker Groups Although derivatives from baseline RRI spectra HRV indices did not differ significantly between groups (FIG. 12B), extensive group differences were found in baseline RRI spectra averaged across groups (FIG. 9). High standard deviation of the mean values of the averaged spectrum in BD group versus the low ones in SD and ND groups did not allow to reveal significant differences in HRV indices between groups. High standard deviation of the averaged RRI spectrum in BD group indicates the heterogeneity of spectral structures. Such heterogeneity could be due to the differences in drinking time periods in BD group.

The values of some cardiovascular parameters in binge drinkers were associated with their Drinking Time Period A significant association between the levels of the VT BRS Gain in young binge drinkers and the duration of their drinking time periods (FIG. 12A) indicates the development of dysregulation of vascular tone at an early stage of binge drinking. Significant correlations between the magnitudes of 0.066 and 0.081 Hz peaks at baseline of RRI spectra in binge drinkers and the duration of their drinking time periods (FIG. 12B) indicates that the value of binge drinking time period influences, in a certain way, the structure of the RRI spectrum. Since the duration of drinking time periods is associated with the levels of VT BRS Gain and, simultaneously, with the structure of RRI spectrum, it was hypothesized that 0.066 and 0.081 Hz peaks at baseline of RRI spectra are linked to VT BRS regulation. It is assumed that HRV in the low-frequency range (0.05-0.15 Hz) is related to baroreflex activity. In accordance with these findings, the low-frequency range of HRV can be divided into two functionally different parts: 1) 0.05-0.08 Hz range that is related to VT BRS and 2) 0.08-0.15 Hz range that is related to HR BRS (FIG. 10). An assumption is made that weakness of the power of RRI spectrum in the range of 0.05-0.08 Hz in binge drinkers reflects the level of endothelial dysfunction.

Example 3

In another example, multiple levels of measurement of multiple cardiovascular processes were studied (also see Table 4). Average function levels in a task as a measure of systemic, metabolic control mechanisms was assessed. Function variability in a task as a measure of the system's capacity to react to change was also assessed. In addition, baroreflex sensitivity as a mechanistic measure of integration across cardiovascular processes was evaluated. The latest level of measurement was focused on process coordination. For example, HR and stroke volume as measures of neural (HR) and muscular (stroke volume) actions of the heart, pulse transit time as a measure of vascular tone, and systolic arterial pressure as the primary measure of blood pressure (BP) were performed. The well-validated standardized indices of cardiovascular function were used to demonstrate cardiac and vascular dysfunction in many mental and physical illnesses and in all-cause mortality. Newly developed strategies were employed to detect subtle preclinical changes. These new strategies, delineated below, are used to differentiate the effects of lifestyle factors, such as binge drinking, on specific control systems and underlying physiological mechanism well prior to the onset disease.

TABLE 4

Physiological Outcome Variables: Ranked (least to most) by Hypothesized Sensitivity to Preclinical Change

| | |
|---|---|
| 1 | Average heart rate, stroke volume, vascular tone, and blood pressure |
| 2 | Heart rate variability, stroke volume variability, vascular tone variability, and blood pressure variability derived using standard spectral indices |
| 3 | Sensitivity (Gain) of heart rate, stroke volume, vascular tone baroreflex branches |
| 4 | Correlation between average heart rate, stroke volume, vascular tone, and blood pressure |
| 5 | Amplitudes of all spectral peaks in the low-frequency range of the HR and PTT spectra |

Binge Drinking Leads to Early Cardiovascular Dysfunction.

Evidence comes from the study that examined the cardiovascular system of social drinkers during the ascending limb of the blood alcohol curve (referred to below as the acute change study) and the study that compared cardiovascular function in the absence of alcohol in non-drinkers, social drinkers, and binge drinkers at rest and during a sympathetic (paced sighing) and parasympathetic (paced breathing) challenge (referred to as the persistent change study).

In the acute change study, those who drank alcohol (peak BAC ~0.08% to mimic a binge episode) vs. juice showed significant elevations in average HR and reductions in average stroke volume. Thus, increased HR occurred in tandem with decreased heart contraction magnitude. This multi-process finding leads to a different interpretation (adaptive adjustment) compared to the single process observation of elevated HR in response to alcohol as has been reported for decades. In the persistent change study, binge and social drinking groups demonstrated only modest, non-significant differences. Thus, each cardiovascular process showed a unique reaction to an acute alcohol challenge, but this did not appear to persist based on a comparison of college-age binge and social drinkers. These changes in average functioning reflect systemic, metabolic influences.

Changes in variability reflect dysfunction in the mechanisms that synchronize the cardiovascular system to other organ systems (e.g., respiratory, neural). FIG. 13A shows the effect size (Cohen's d) of pre- to post-beverage changes in cardiovascular variability (d>0 implies increases, d<0 implies decreases). Alcohol-related reductions in variability were noted in HR (HF HRV=high-frequency HRV; LF HRV=low-frequency HRV), stroke volume (SVV), pulse transit time (PTTV, an index of vascular tone variability), and BP (BPV). Less variability in the system implies more rigidity. In the persistent change study, a consistent pattern of subtle, albeit non-significant, reductions were noted in the binge versus social drinking groups, suggesting subtle effects of intoxication that are not yet permanent. Thus, cardiovascular variability was reduced during an acute alcohol challenge, but this reduction did not appear to persist based on comparison of college-age binge and social drinkers.

In the acute change study, blood vessels reacted more strongly to a 1-unit change in BP after, compared to before, alcohol was consumed (FIG. 13B). Thus, during the ascending limb of the blood alcohol curve, the vasculature was hypersensitive, pressure and flow were more tightly linked, and/or the sympathetic nervous system was more activated. This last possibility implies that binge drinking may reduce parasympathetic activity and increase sympathetic activity, creating two parallel pathways of system loading. It also suggests that blood vessels are particularly quick to detect the presence of alcohol and preemptively activated to offset alcohol's suppressive effects on the cardiovascular system following oral consumption. In the persistent change study, in the absence of intoxication, blood vessels reacted less strongly to a 1-unit change in BP in binge versus social drinkers. Thus, vascular tone baroreflex sensitivity was increased during acute alcohol intoxication, but reduced when comparing binge drinkers to social drinkers.

Figure 14:
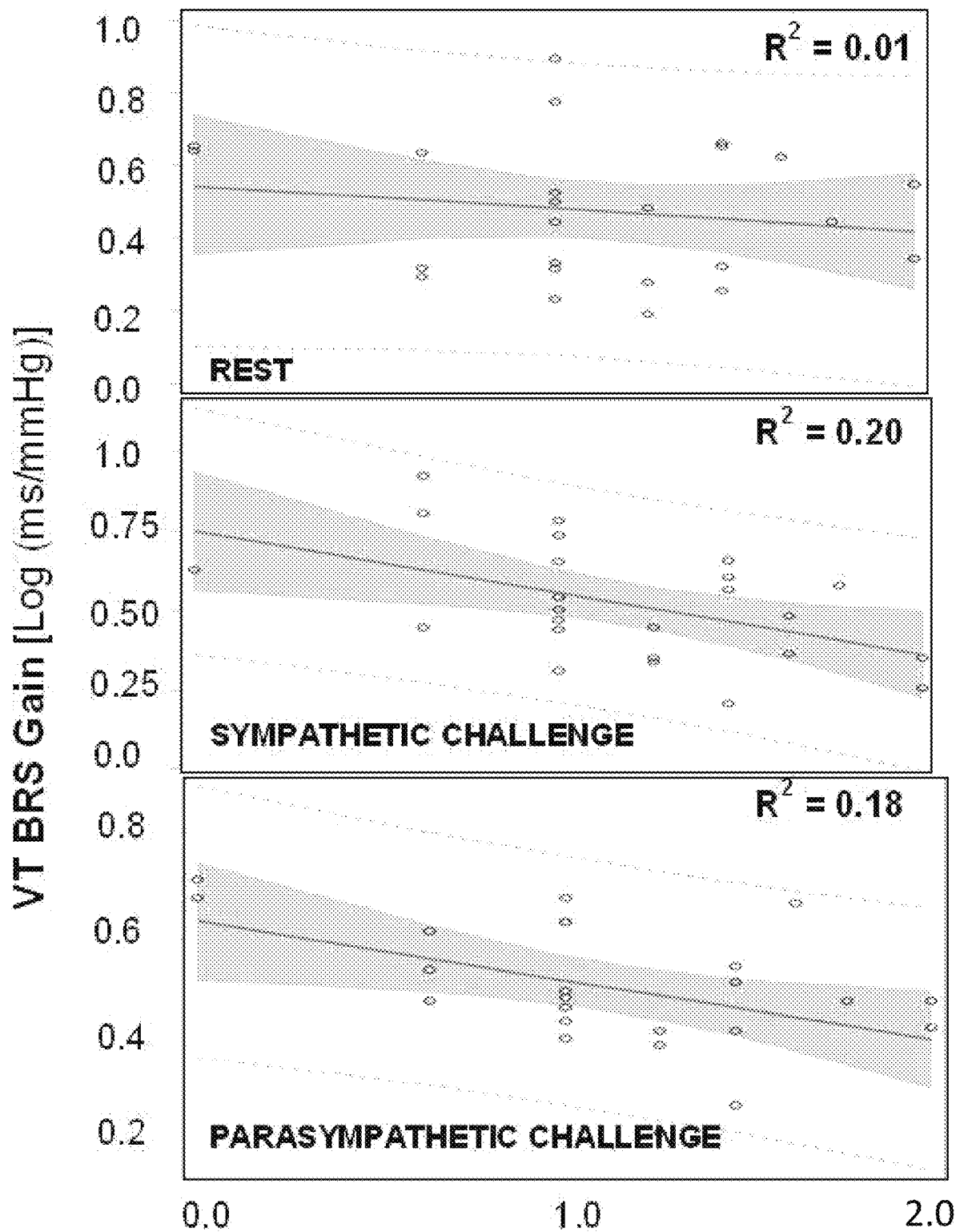
FIG. 14 shows a correlation of vascular tone baroreflex sensitivity with years of alcohol use in binge drinkers.

Further, FIG. 13C shows the sensitivity of the vascular tone baroreflex in the unchallenged rest state (B1), during a sympathetic challenge (S30, paced sighing) and a parasympathetic challenge (6P, paced breathing) of binge and social drinkers. At rest, local vascular control systems (i.e., endothelial) are tonically active. As loading increases and the system is taxed, central control systems (i.e., baroreflex) come online to supplement these tonic systems. This is seen as magnified group differences in baroreflex sensitivity under conditions of system loading. FIG. 14 shows that VT baroreflex sensitivity was negatively associated with years of alcohol exposure, during system loading (middle and bottom) but not at rest (top). Thus, in the persistent change study, reductions in vascular tone baroreflex sensitivity in binge drinkers were associated with drinking history.

Not only does alcohol exert independent effects on HR, stroke volume, vascular tone and BP, but it changes the relationship of these processes to each other. In the acute change study, Changes in pulse transit time (ΔPTT; Y-axis)—a measure of vascular tone—in relation to changes in HR (FIG. 15A), stroke volume (ΔSV, FIG. 15B), and BP (FIG. 15C) were also observed (FIG. 15). In all cases, alcohol exerted large-scale effects on the heart and vessels compared to juice. Individual variability in the alcohol group is notable in terms of vascular change (Y-axis), with some showing vasodilation (increases in PTT) and others showing vasoconstriction. Individual variability in changes in HR, stroke volume, and BP were also large. Another way to view these interrelations is by plotting significant correlations between the processes (FIG. 16A). Both figures illustrate that alcohol intoxication instigates system-wide coordination, likely an adaptive response to ensure that an acute insult to any element (e.g., the heart muscle or vessel walls) can be efficiently managed. In the persistent change study, young adult binge drinkers who were not intoxicated still showed greater coupling between cardiovascular processes at rest and during challenges than the non-drinking or social drinking groups (FIG. 16B). Thus, the relationships of cardiovascular processes to each other was changed in the presence of alcohol, and this change was also observed in young adult binge drinkers compared to social drinkers and non-drinkers.

The data presented herein demonstrate widespread cardiovascular effects of a binge-like drinking episode (acute change study) and evidence that some of these effects are present in sober individuals who repeatedly engage in binge drinking (persistent change study). This study was aimed not only to create a framework for understanding how the vasculature responds alcohol, but also to capture binge drinking "dose" multi-dimensionally in order to address subtleties of alcohol use behaviors nor the potential for cumulative effects.

Novel Methods for Measuring and Manipulating the Cardiovascular System.

Cardiac control is mediated in part by inputs from the parasympathetic and sympathetic nervous system to the sinoatrial node in the heart. Vascular control is mediated only via input from the sympathetic nervous system. Challenge tasks were developed to characterize these distinct neural inputs and to measure the mechanisms underlying binge drinking-related cardiovascular change.

Most research on cardiac control systems focuses on the parasympathetic nervous system, which is primarily mediated through the vagus nerve (Cranial Nerve X) and is measurable through phenomena such as respiratory sinus arrhythmia (RSA) that links HR to respiration (acceleration→inhalation, deceleration→exhalation). The method presented herein for instantaneously provoking parasympathetic activity is also called resonance breathing. The method paces breathing to 0.1 Hz (6 breaths/min) to align cardiac oscillations driven by RSA with cardiac oscillations driven by the HR baroreflex, which naturally occur at 0.1 Hz because this closed-loop system has a 5-sec delay between a BP change and a corresponding change in HR that creates a 10 sec or 0.1 Hz cycle. External stimulation of the system at 0.1 Hz (e.g., with breathing) synchronizes two cardiac control processes and elicits a resonance response (small input 4 large output). Resonance breathing performed instantaneously induced large oscillations in HR (but negligible changes in average HR) reduced systolic BP and increased baroreflex sensitivity. Resonance breathing is experienced as relaxing and has many empirically-supported clinical uses—the parasympathetic/vagal system is considered the 'rest and digest' nervous system. Resonance breathing was used as a parasympathetic challenge to measure parasympathetic cardiac control.

A key problem with provoking sympathetic activation is that the closed-loop circuit that links vascular tone to BP has a longer delay. The time it takes for a change in BP to influence the vasculature across the body and for vasoconstriction/vasodilation to feedback to BP control systems is likely 15 sec or longer. Based on knowledge of well-established cardiorespiratory control mechanisms (e.g., respiratory sinus arrhythmia) and the fact that most individuals cannot comfortably breath slower than 6 breaths per min (~½-⅓ of typical breathing rate), the use of sighing to provoke sympathetically-mediated cardiovascular change was explored. Early studies in the field showed that both spontaneous and voluntary sighs restored structured respiratory variability when it was disturbed by stress, emotions, or sustained attention. Using this information, a paced sighing task where participants breathed normally except when cued to perform a voluntary sigh at certain frequencies is disclosed. Three sighing frequencies: once every 50 sec (0.02 Hz), 30 sec (0.033 Hz), and 15 sec (0.066 Hz) were tested.

Like resonance breathing, repeated sighing imposed oscillations in all studied cardiovascular processes at that frequency without provoking major increases in average HR, stroke volume, pulse transit time, or diastolic BP (which implies provocation of neural control systems with limited influence on metabolic control systems). Moreover, paced sighing was ideal for instantaneously provoking sympathetic activity. Each sigh elicited a strong and immediate increase in skin conductance, a purely sympathetic physiological system. This sympathetic response showed no signs of habituation across the 5-minute task when sighs were paced once every 30 sec or once every 15 sec. In Fourier transformation of the RRI data, a large amplitude peak was observed at 0.066 Hz, the frequency at which this participant was sighing. This peak is not observed at rest. Paced sighing was used as a sympathetic challenge to measure sympathetic cardiac control and baroreflex-mediated vascular control.

Figure 17:
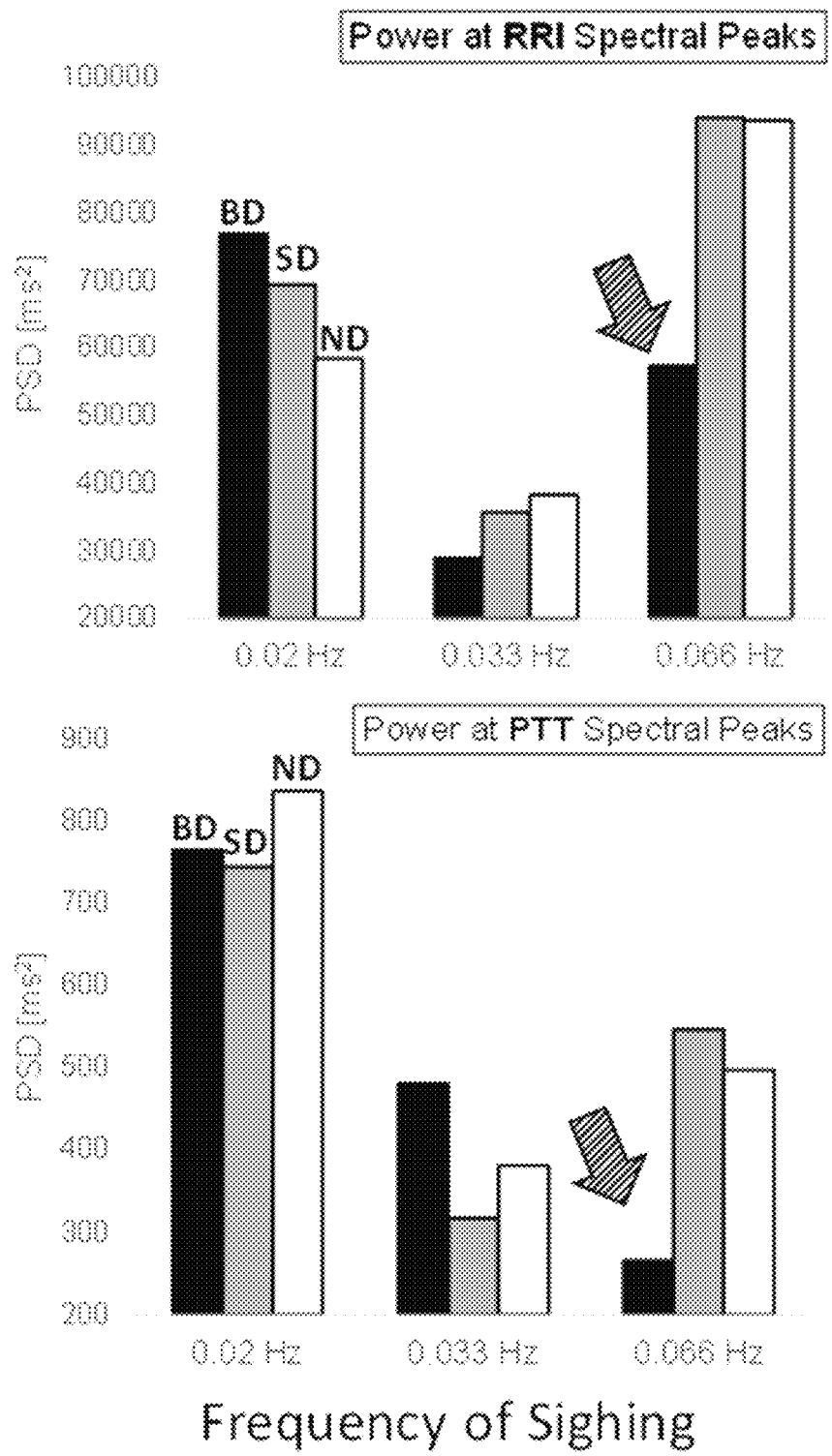
FIG. 17 shows PSD values of RRI and PTT spectral peaks of ND, SD, and BD in paced sighing tasks at 0.02, 0.033, and 0.066 Hz. Striped arrows indicate statistically significant reductions in peak amplitude.

It has been shown that (a) the magnitude of a sympathetic challenge can be controlled by changing the pace of sighing and (b) the shape of the resting HR and vascular tone spectra, in the low-frequency domain, were useful in differentiating HR and vascular tone control systems that arise from sympathetic input. As stated above, each sigh elicited a strong reaction across cardiovascular processes that did not habituate. When time-series data from a 5-minute epoch of paced sighing was Fourier transformed, the resulting spectra showed large amplitude spectral peaks at the testing frequency. FIG. 17 plots the amplitude of these peaks separately for binge drinkers (BD), social drinkers (SD), and non-drinkers (ND). Sighing once every 50 sec or every 30 sec led to similar amplitude peaks at 0.02 Hz in all groups in both the HR (RRI; top) and vascular tone (PTT; bottom) spectra. However, when sighing frequency was increased to once every 15 sec, the binge drinking group showed dramatic and statistically significant reductions in peak amplitude (striped arrow). The challenge to biological systems transiently perturbs functioning that gradually recovers. If challenges occur too frequently, however, the system may not have sufficient time for fully recovery. The diminished low-frequency spectral peaks in binge drinkers may indicate longer recovery from a challenge. Thus, paced sighing may be a sensitive, preclinical indicator of cardiovascular dysfunction related to loss of arterial elastance.

Figure 18:
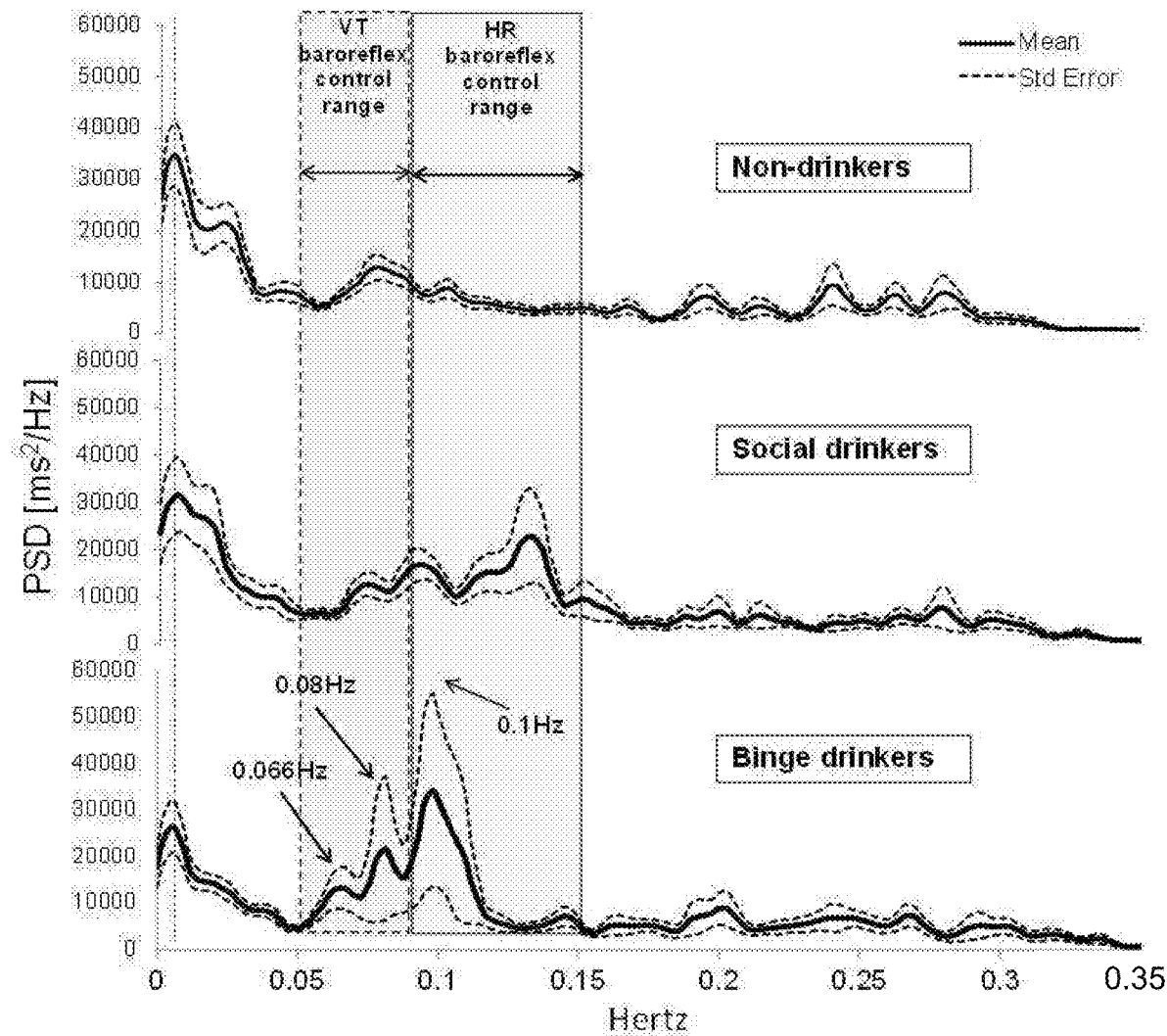
FIG. 18 shows readily observable differences in spectral structure in the low-frequency range (0.05-0.15 Hz) of ND (top), SD (middle), and BD (bottom).
Figure 19:
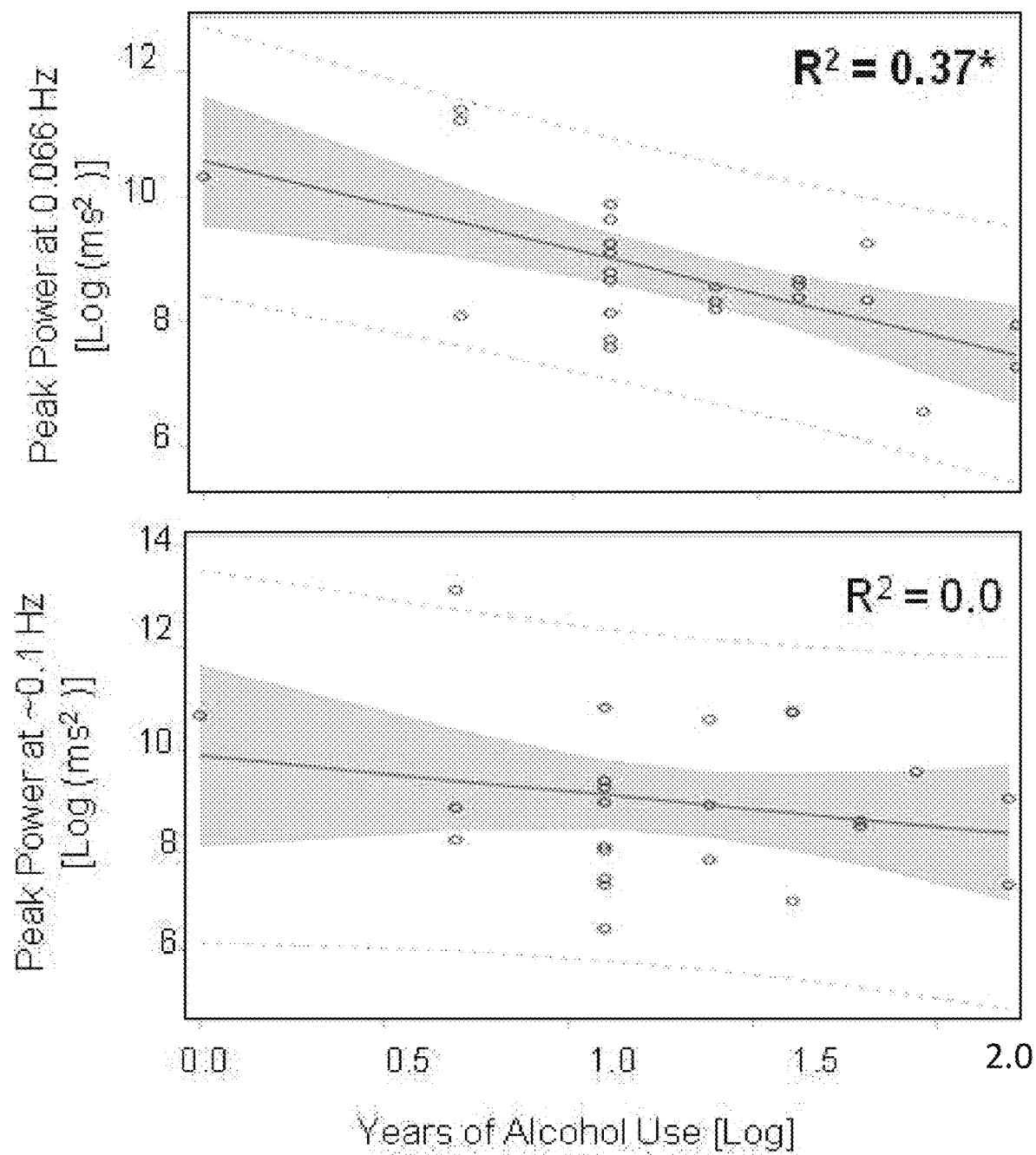
FIG. 19 shows a correlation between power at 0.066 Hz (vascular/sympathetic) with the history of alcohol use in the BD group.

Further evidence of sustained, preclinical cardiovascular change comes from examining group-averaged baseline HR spectra. FIG. 18 shows readily observable differences in spectral structure in the low-frequency range (0.05-0.15 Hz) of non-drinkers (top), social drinkers (middle), and binge drinkers (bottom). Participants were not performing paced tasks; thus, evidence of low-frequency power peaks was unexpected. It was previously proposed that the ~0.1 Hz peak reflects chronically active HR control systems and the 0.066 Hz peak reflect chronically active vascular tone control systems. Quantification of low-frequency power peaks in baseline HR spectra may be a sensitive indicator of preclinical, binge drinking-related cardiovascular change in college students. FIG. 19 shows that power at 0.066 Hz (vascular/sympathetic), but not 0.1 Hz (cardiac/parasympathetic), was related to the history of alcohol use in the binge drinking group.

2. Methods

Subjects and Recruitment.

300 first year students (17-21 years) will be recruited using multiple strategies in collaboration with the university's Health Outreach, Promotion, and Education office. Recruitment opportunities include: (a) information session/table at student orientation sessions held the summer prior to admission, (b) the university's Involvement Fair, held Labor Day weekend after move-in but prior to class start. The fair hosts >500 organizations, clubs, departments, and community partners to let students learn about opportunities across campus; and (c) via one of two surveys administered to incoming Rutgers University students (alcohol.edu and the National College Health Assessment) that allow participants to opt-in to be contacted about future research initiatives at the university. Only name and method of contact will be provided to the research team. Interested individuals will then be contacted by the Cardiac Neuroscience Laboratory staff, who will determine eligibility from a brief telephone interview. Participants will be recruited in Years 1 and 2 to allow all initial laboratory testing during the fall semester. Thus, there will be two cohorts of first-year college students (n=150 per year). Years 3 and 4 will be used to retest participants during their $3^{rd}$ year (20% attrition, n=120 per year).

Inclusion/Exclusion Criteria.

Physically healthy, normotensive individuals who are entering college or in their first year of college will be included. Exclusion criteria are high blood pressure (>140/90 mmHg) and medical conditions that directly or indirectly influence cardiovascular functioning (e.g., diabetes, cardiac arrhythmia), medications affecting the cardiovascular system, and a body mass index greater than 35 (severely obese), or overt psychosis. Use of other drugs and/or prior diagnosis of a substance use disorder will not serve as exclusion criteria, but careful screening will ensure the ability to assess the moderating influences of these factors. There are no exclusion criteria based on sex or race/ethnicity. Males and females will be recruited in sufficient numbers to allow for assessment of sex differences.

Questionnaires.

Questionnaires include demographics, a comprehensive health and lifestyles checklist containing personal history of physical and mental health disorders, health problems, physical conditions, body mass index, exercise and sleep habits, familial diagnoses of SUD and cardiovascular disease, other drug use behaviors, Rutgers Alcohol Problem Index, Beck Depression Inventory II, Beck Anxiety Inventory, Perceived Stress Scale (PSS-10), the Penn State Worry Questionnaire and a modified Important Persons and Activities instrument. Comprehensive assessment of alcohol use will be captured at the laboratory sessions using standard quantity/frequency/recency measures, the age of first use, with 2 weeks, past year, and lifetime time scales. This survey also asks items about drinking patterns (i.e., shots) and typical beverage consumed.

Physiological Tasks.

Baseline (5 min): a low cognitive demand 'Vanilla' task to equate mental activity across individuals, Low sympathetic challenge (5 min): a paced sighing task that involves natural breathing interspersed with a voluntary short, rapid and deep breath (i.e., a sigh) once every 30 sec (0.033 Hz) as cued by the TV screen turning red (E-Prime program; Psychology Software Tools, Inc., Pittsburgh, Pa.), High sympathetic challenge (5 min): a paced sighing task like #2 but paced once every 15 sec (0.066 Hz), Parasympathetic challenge (5 min): a paced breathing task that slows breathing (typically 12-20 breathes per min) to six breathing cycles per min (0.1 Hz) using a visual pacer (Easy Air, Biofeedback Foundation of Europe, Montreal, Canada) presented on the TV screen, and Cognitive challenge (5 min): the Stroop Color Word Test, where the printed name and ink color of a color word differ (e.g., the word "green" written in red ink), will be presented on the TV screen. Participants will use a modified keyboard where the arrow keys are overlaid with green, red, blue, and yellow squares and asked to press the appropriate key based on the ink color of the word, not the color name (e.g., select the red key when the word "green" is written in red ink). Speed and accuracy will be recorded.

Figure 20:
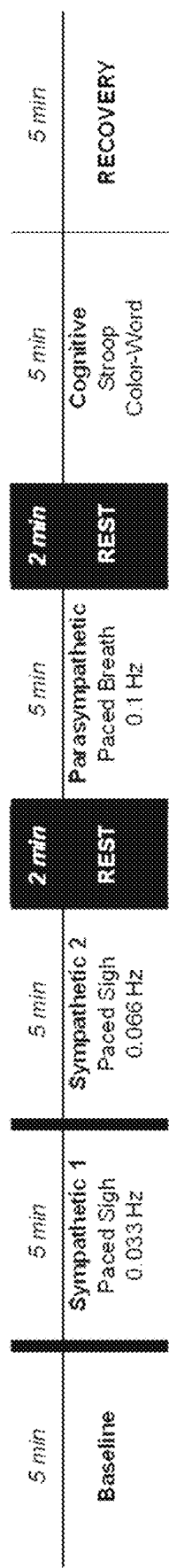
FIG. 20 shows an order of physiological tasks completed during the in-lab experiment.

FIG. 20 shows the overall task sequence. A 30-sec inter-task interval will occur between the baseline and sympathetic tasks whereas 2-min inter-task rest/recovery periods will occur between tasks that activate different control centers. The recording will continue after the cognitive challenge to measure recovery to baseline. Prior to the initiation of the full study, a pilot study was conducted to ensure that there were sufficient 'wash-out' periods between the parasympathetic and sympathetic challenges and determine the feasibility of counterbalancing these tasks. The cognitive challenge will remain last to allow monitoring recovery time course.

Physiological Measurement.

A respiration strain gauge belt will be placed around the chest. A BP cuff will be placed on the second phalange of the middle finger (non-dominant hand). A standard lead II configuration for electrocardiogram (ECG) recording will be used. A PowerLab Acquisition System (ADInstruments, Colorado Springs, Colo.) will collect ECG and respiration. A Finometer MIDI (Finapres Medical Systems, Netherlands) will collect beat-to-beat arterial BP. A sample rate of 2000/sec will be used.

Laboratory Procedures.

Participants will complete about a 1.5 hour experimental session (10 am-2 pm to minimize biological circadian variations) at the Rutgers Cardiac Neuroscience Laboratory. Written informed consent will be obtained upon arrival. Breath analysis will confirm zero blood alcohol, and urine screens will confirm drug use self-reports. Questionnaires will be completed. Participants will be comfortably seated 2.5 minute in front of a large TV screen in a sound attenuated, dimly lit room. ECG, beat-to-beat blood pressure, and thoracic respiration will be collected during all tasks detailed in FIG. 20. Following completion of the tasks, physiological recording sensors will be removed. Participants will be given a unique personal identification number (i.e., PIN) that will be entered every time they complete a survey. When possible, this PIN will be entered into the Notes app (standard on all iPhones). The Note will only say, e.g., '1234' and will not be associated with the research study. The staff will send a practice text message with a practice survey link. Participants will complete a practice survey with the staff to ensure that they understand all items and the methods being used.

2.1. Analytic Strategies

Physiological Analyses:

Physiological reactions to each task (baseline, sympathetic challenges, parasympathetic challenge, cognitive challenge tasks, and cognitive recovery period) will be analyzed separately. WinCPRS software (Absolut Aliens Oy, Finland) will measure the sequence of RR intervals (RRI) from the ECG, stroke volume, beat-to-beat pulse transit time (PTT, interval between the R wave of the ECG and the apex of the corresponded BP wave), and beat-to-beat systolic, diastolic and mean arterial pressure (SAP, DAP, and MAP)

Spectral Analysis.

Using Fourier transformation, frequency spectra of RRI, SAP, DAP, MAP, and PTT will be calculated. Power at all peaks in the low-frequency range of the HR and PTT spectra will be calculated for each participant individually.

Cross-Spectral Analysis.

Transfer functions (TF) between SAP (input) and PTT (output) [TF(SAP-PTT)] or RRI (output) [TF(SAP-RRI] will be calculated. VT and HR BR gain will be measured as average TF(SAP-PTT) and TF(SAP-RRI), respectively, in frequency ranges where is coherence >0.5. The gain will also be calculated separately at each testing frequency and in the low (LF; 0.005-0.15 Hz) and high (HF; 0.15-0.5 Hz) frequency ranges. The correlations between average responses of each cardiovascular process will be computed and graphed to assess system coupling.

Statistical Analyses: Analyses Will be Performed with SAS 9.4 (SAS Institute Inc., Cary, N.C.) and MPlus.

Exemplary System Architecture

Figure 21:
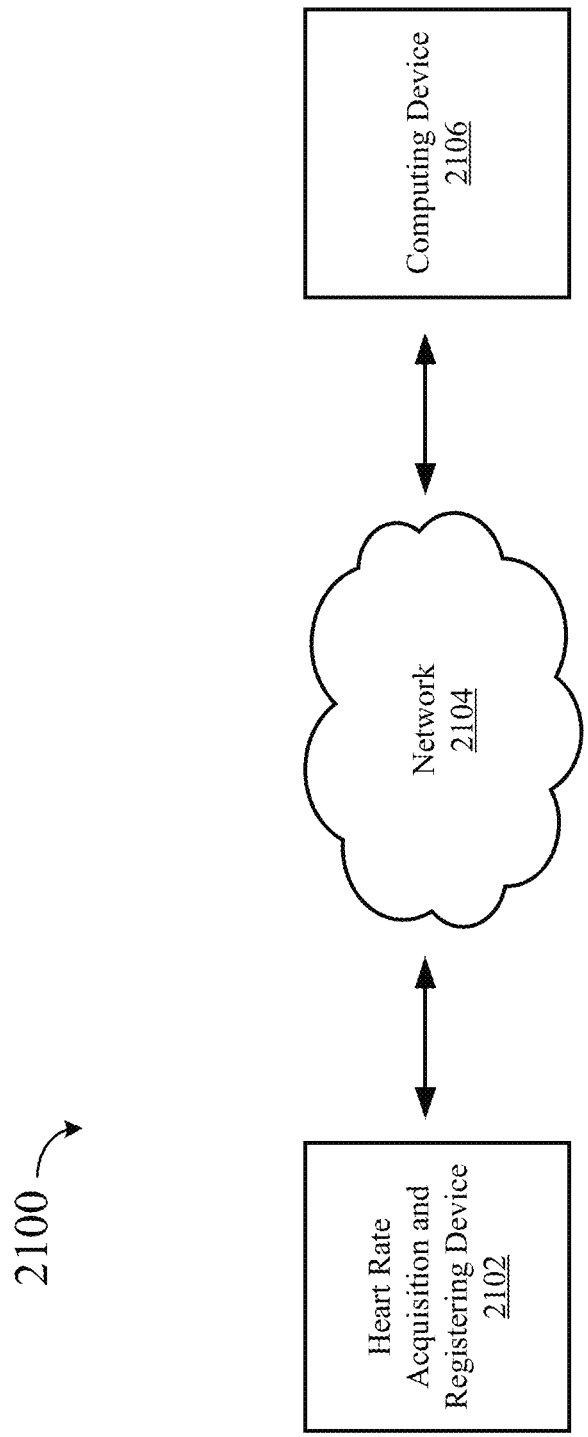
FIG. 21 is an illustration of an exemplary architecture for a system.

Referring now to FIG. 21, there is provided an illustration of an exemplary architecture for a system 2100 in which the present solution can be implemented. System 2100 comprises a heart rate acquisition and registering device 2102 communicatively coupled to a computing device 2106 via a network 2104 (e.g., the Internat or Intranet). Computing device 2106 includes, but is not limited to, a personal computer, a laptop computer, a desktop computer and/or a server. Accordingly, the computing device 2106 comprises one or more output devices (e.g., a display screen, a speaker and/or a vibrator) to output a rhythmical visual, auditory and/or tactile signals to perform a plurality of sighs by a subject. An exemplary architecture of the computing device 2106 is discussed in detail below in relation to FIG. 19.

During operation, the heart rate acquisition and registering device 2102 performs operations to: acquire heart rate data from one or more sensors disposed in proximity to the subject; and/or register the subject's heart's electrical activity via an ECG, PhotoPlethysmoGraphic ("PPG") signals and/or light via a device that is capable of performing physiologic monitoring (e.g., a mobile phone executing a software application). Method for ECG and PPG registration are well known in the art, and therefore will not be described herein. Any known or to be known ECG and/or PPC registration process can be used without limitation. The computing device then performs heartrate signal processing, Fourier spectral analysis, and result collection. These operations can involve the process described above in 204 of FIG. 2. Thereafter, the results of the vessel elasticity evaluation are feedback via the output device(s) of the computing device (e.g., displayed on a display screen). The vessel elasticity evaluation can involve the process described above in relation to 214 of FIG. 2.

Figure 22:
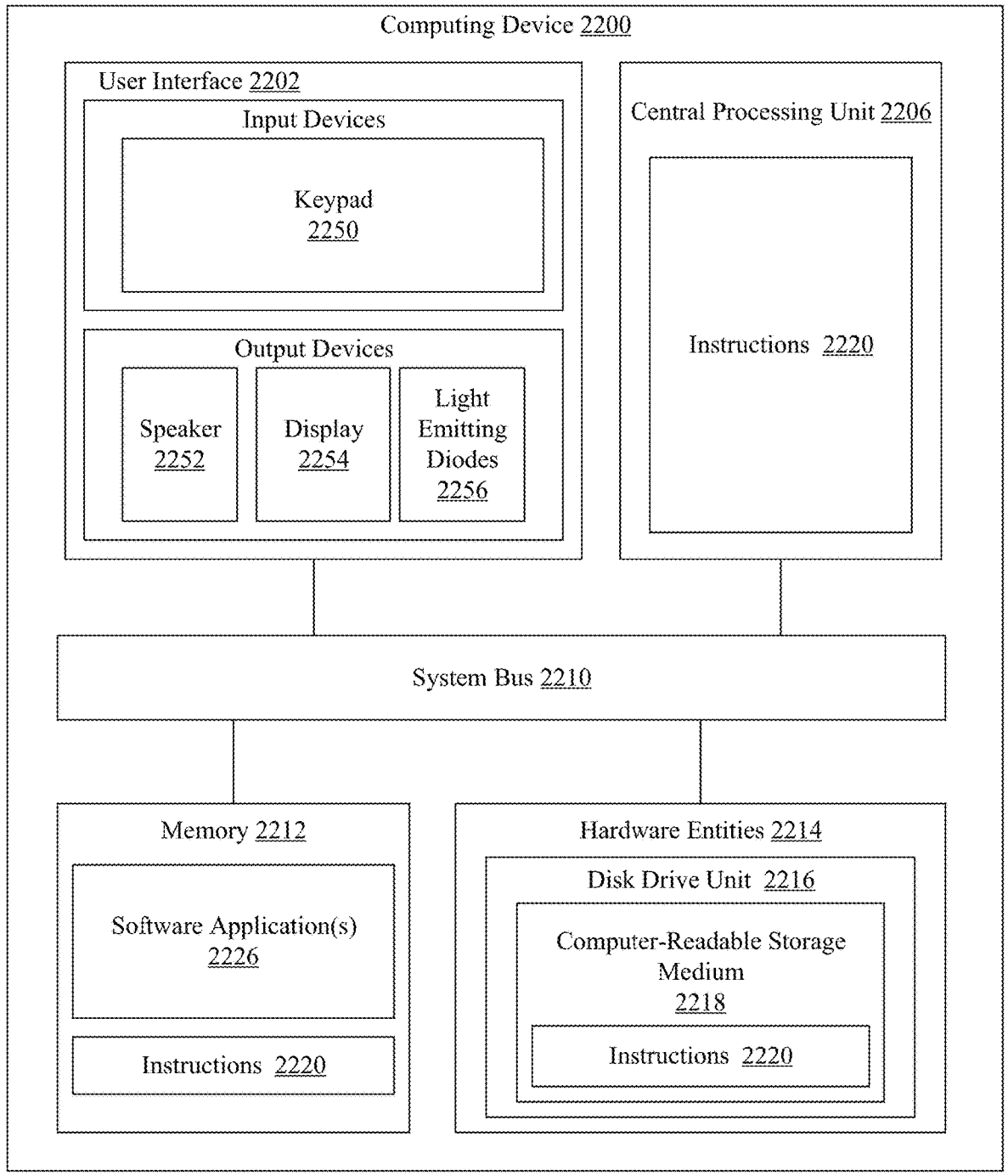
FIG. 22 is an illustration of an exemplary architecture for a computing device.

Referring now to FIG. 22, there is provided a detailed block diagram of an exemplary architecture for a computing device 2200. Computing device 2106 of FIG. 21 is the same as or substantially similar to computing device 2200. As such, the following discussion of computing device 2200 is sufficient for understanding computing device 2106 of FIG. 21.

Computing device 2200 may include more or fewer components than those shown in FIG. 22. However, the components shown are sufficient to disclose an illustrative embodiment implementing the present solution. The hardware architecture of FIG. 22 represents one embodiment of a representative computing device configured to facilitate express estimation of arterial elasticity. As such, the computing device 2200 of FIG. 22 implements at least a portion of a method for express estimation of the arterial elastic property in a person.

Some or all the components of the computing device 2200 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 22, the computing device 2200 comprises a user interface 502, a Central Processing Unit ("CPU") 2206, a system bus 2210, a memory 2212 connected to and accessible by other portions of computing device 2200 through system bus 2210, and hardware entities 2214 connected to system bus 2210. The user interface can include input devices (e.g., a keypad 2250) and output devices (e.g., speaker 2252, a display 2254, and/or light emitting diodes 2256), which facilitate user-software interactions for controlling operations of the computing device 2200.

At least some of the hardware entities 2214 perform actions involving access to and use of memory 2212, which can be a RAM, a disk driver and/or a Compact Disc Read Only Memory ("CD-ROM"). Hardware entities 2214 can include a disk drive unit 2216 comprising a computer-readable storage medium 2218 on which is stored one or more sets of instructions 2220 (e.g., software code) configured to implement one or more of the methodologies, procedures, or functions described herein. The instructions 2220 can also reside, completely or at least partially, within the memory 2212 and/or within the CPU 2206 during execution thereof by the computing device 2200. The memory 2212 and the CPU 2206 also can constitute machine-readable media. The term "machine-readable media," as used here, refers to a single medium or multiple media (e.g., a centralized or distributed database, and/or associated caches and servers) that store the one or more sets of instructions 2220. The term "machine-readable media," as used here, also refers to any medium that is capable of storing, encoding or carrying a set of instructions 2220 for execution by the computing device 2200 and that causes the computing device 2200 to perform any one or more of the methodologies of the present disclosure.

In some scenarios, the hardware entities 2214 include an electronic circuit (e.g., a processor) programmed for facilitating the provision of item-level information in a language and currency used in a given geographic location whereat or wherein an EST or ESL resides. In this regard, it should be understood that the electronic circuit can access and run an item level information management application 2224 installed on the computing device 2200. Functions of the software application 2226 are apparent from the above discussion.

Although the present solution was described above as a means to estimate vascular dysfunction as a result of hazardous alcohol use, other uses are contemplated. For example, an estimate of arterial elasticity can also be useful as an indicator of healthy/normal vascular tone (that is, normal function) vs. dysfunction when a determined value is less than a specified threshold. The threshold value may be selected based on a value appropriate for a given age of the subject. Besides, the present solution allows one to monitor the level of personal arterial elasticity indicative of stress, hypertension, and other cardiovascular problems. Even furthermore, the estimate may be used as "an indicator of stress" or cardiovascular problems.

The threshold value can be defined as the average PSD of a specific frequency (within the frequency range 0.06 Hz-0.08 Hz, and corresponding to the frequency of paced sighing being performed during the time period of heart rate recording) determined from a healthy population within an age and/or gender group. Further, the average PSD of the healthy young population can be taken as the universal threshold value, so healthy old individual will have a lower PSD as compared to the threshold value and thus a lower arterial elasticity.

The present solution may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

As used in this document, the singular form "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values.

All of the apparatus, methods, and algorithms disclosed and claimed herein can be made and executed without undue experimentation in light of the present disclosure. While the invention has been described in terms of preferred embodiments, it will be apparent to those having ordinary skill in the art that variations may be applied to the apparatus, methods, and sequence of steps of the method without departing from the concept, spirit, and scope of the invention. More specifically, it will be apparent that certain components may be added to, combined with, or substituted for the components described herein while the same or similar results would be achieved. All such similar substitutes and modifications apparent to those having ordinary skill in the art are deemed to be within the spirit, scope, and concept of the invention as defined.

The features and functions disclosed above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

What is claimed is:

1. A method for assessing arterial elasticity, imposing a rhythmical stimulation to cause an oscillation on the cardiovascular system of a subject,
   wherein the rhythmical stimulation is induced by causing the subject perform a paced sighing at a pacing frequency of about 0.066 Hz or about 0.081 Hz;
   measuring each of the paced sighing beat-to-beat intervals and pulse transit time (PTT) responses that are associated with the oscillation on the cardiovascular system of the subject caused by the rhythmical stimulation;
   generating a frequency spectrum for the measured beat-to-beat intervals and PTT responses; and determining an arterial elasticity of the subject by determining heart rate variability (HRV) based on amplitudes of the beat-to-beat intervals and PTT response associated with the oscillation at the pacing frequency in the frequency spectrum.

2. The method of claim 1, wherein the step of imposing the rhythmical stimulation comprises:
   providing the subject a rhythmical reference cue; and
   causing the subject to perform the paced sighing in response to the rhythmical reference cue, whereby the paced sighing imposes the rhythmical stimulation on the cardiovascular system of the subject.

3. The method of claim 2, wherein the rhythmical reference cue is a visual cue, an audio cue or a tactile cue.

4. The method of claim 1, wherein the step of measuring the response associated with the oscillation comprises:

generating an equidistant waveform based on the beat-to-beat intervals; and generating a frequency domain spectrum from the equidistant waveform by a fast Fourier transform (FFT).

5. The method of claim 4, wherein the step of generating the equidistant waveform comprises:

performing cubic interpolation for the beat-to-beat intervals of the subject; and resampling the interpolated beat-to-beat intervals at a rate of 4 Hz.

6. The method of claim 4, wherein the beat-to-beat intervals are measured from a signal from an electrocardiogram (ECG or EKG), plethysmograph, or photoplethysmography (PPG).

7. The method of claim 4, wherein the step of determining the arterial elasticity of the subject comprises determining a power spectrum density of the frequency domain spectrum at a reference frequency.

8. The method of claim 1, wherein the rhythmical stimulation is a sympathetic challenge.

9. The method of claim 8, wherein the sympathetic challenge is a paced sighing sympathetic challenge.

10. A method of evaluating an impact of alcohol consumption on a subject, wherein evaluation of an impact of alcohol consumption is based on a correlation between a drinking profile and the assessment of the arterial elasticity according to claim 1, the drinking profile comprising years of alcohol use of the subject.

11. A system for assessing arterial elasticity, comprising:
a non-transitory, computer readable memory;
one or more processors; and
a computer-readable medium containing programming instructions that, when executed by the one or more processors, cause the system to:

impose a rhythmical stimulation to cause an oscillation on the cardiovascular system of a subject, wherein the rhythmical stimulation is induced by causing the subject to perform a paced sighing at a pacing frequency of about 0.066 Hz or about 0.081 Hz;

measure each of the paced sighing beat-to-beat intervals and PTT responses that are associated with the oscillation on the cardiovascular system of the subject caused by the rhythmical stimulation;

generate a frequency spectrum for the measured beat-to-beat intervals and PTT responses; and determine an arterial elasticity of the subject by determining heart rate variability (HRV) based on amplitudes of the beat-to-beat intervals and PTT responses associated with the oscillation at the pacing frequency in the frequency spectrum.

12. The system of claim 11, further comprising programming instructions, when executed by the one or more processors, causing the system to:

provide the subject a rhythmical reference cue; and cause the subject to perform the paced sighing to the rhythmical reference cue, whereby the paced sighing imposes the rhythmical stimulation on the cardiovascular system of the subject.

13. The system of claim 11, further comprising programming instructions, when executed by the one or more processors, causing the system to:

generate an equidistant waveform based on the beat-to-beat intervals; and generate a frequency domain spectrum from the equidistant waveform by a fast Fourier transform (FFT).

14. The system of claim 11, further comprising programming instructions, when executed by the one or more processors, causing the system to:

perform cubic interpolation for the beat-to-beat intervals of the subject; and resample the interpolated beat-to-beat intervals at a rate of 4 Hz.

15. The system of claim 11, further comprising programming instructions, when executed by the one or more processors, causing the system to determine a power spectrum density of the frequency domain spectrum at a reference frequency.

16. The system of claim 11, wherein the rhythmical stimulation is a paced sighing sympathetic challenge.

* * * * *

UNITED STATES PATENT AND TRADEMARK OFFICE
CERTIFICATE OF CORRECTION

PATENT NO. : 11,076,762 B2
APPLICATION NO. : 15/919757
DATED : August 3, 2021
INVENTOR(S) : Evgeny G. Vaschillo et al.

It is certified that error appears in the above-identified patent and that said Letters Patent is hereby corrected as shown below:

In the Claims

At Column 28, Claim number 1, Line number 40, add the word "comprising:" after the word "elasticity".

At Column 28, Claim number 1, Line number 44, add the word "to" after the word "subject".

At Column 30, Claim number 14, Line number 25, delete the entire claim and add in its place:
"A system for assessing arterial elasticity, comprising:
    a non-transitory, computer readable memory;
    one or more processors; and
    a computer-readable medium containing programming instructions that, when executed by the one or more processors, cause the system to:
    impose a rhythmical stimulation to cause an oscillation on the cardiovascular system of a subject, wherein the rhythmical stimulation is induced by causing the subject to perform a paced sighing at a pacing frequency of about 0.066 Hz or about 0.081 Hz;
    measure each of the paced sighing beat-to-beat intervals and PTT responses that are associated sighing at a pacing frequency of about 0.066 Hz or about 0.081 Hz;
    measure each of the paced sighing beat-to-beat intervals and PTT responses that are associated with the oscillation on the cardiovascular system of the subject caused by the rhythmical stimulation;
    generate a frequency spectrum for the measured beat-to-beat intervals and PTT responses; and
    determine an arterial elasticity of the subject by determining heart rate variability (HRV) based on amplitudes of the beat-to-beat intervals and PTT responses associated with the oscillation at the pacing frequency in the frequency spectrum."

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*